(12) United States Patent
Pilkington et al.

(10) Patent No.: US 10,702,629 B2
(45) Date of Patent: Jul. 7, 2020

(54) CONDITIONING HARVESTED FAT FOR RE-INJECTION

(71) Applicant: Black Tie Medical Inc., San Diego, CA (US)

(72) Inventors: Mary L. Pilkington, San Diego, CA (US); Mariano C. Riego de Dios, San Diego, CA (US)

(73) Assignee: Black Tie Medical Inc., San Diego, CA (US)

( * ) Notice: Subject to any disclaimer, the term of this patent is extended or adjusted under 35 U.S.C. 154(b) by 290 days.

(21) Appl. No.: 15/675,329

(22) Filed: Aug. 11, 2017

(65) Prior Publication Data

US 2017/0368226 A1    Dec. 28, 2017

Related U.S. Application Data

(63) Continuation-in-part of application No. 15/154,885, filed on May 13, 2016, and a continuation-in-part of
(Continued)

(51) Int. Cl.
*A61L 27/36* (2006.01)
*B01D 17/02* (2006.01)
(Continued)

(52) U.S. Cl.
CPC .......... *A61L 27/3687* (2013.01); *A61K 35/35* (2013.01); *A61L 27/3604* (2013.01);
(Continued)

(58) Field of Classification Search
None
See application file for complete search history.

(56) References Cited

U.S. PATENT DOCUMENTS

| | | | | |
|---|---|---|---|---|
| 4,753,634 A | * | 6/1988 | Johnson | A61B 17/34 210/406 |
| 4,834,703 A | * | 5/1989 | Dubrul | A61B 10/02 604/48 |

(Continued)

OTHER PUBLICATIONS

U.S. Appl. No. 62/207,746 to Bradford A. Conlan filed Aug. 20, 2015.
(Continued)

*Primary Examiner* — Robert J Popovics
(74) *Attorney, Agent, or Firm* — Rodney F. Brown

(57) ABSTRACT

A fat conditioning apparatus includes a conditioning vessel enclosing a conditioning chamber and a displacable plug. The conditioning chamber is bounded on one end by the displacable plug and has a variable volume that is a function of the position of the plug within the conditioning vessel. The apparatus has utility in a fat conditioning method, wherein the conditioning chamber contains a harvested fat emulsion. A washing liquid is injected into the conditioning chamber and mixes with the harvested fat emulsion, thereby displacing the plug in an outward expansion direction and expanding the variable volume of the conditioning chamber. The resulting mixture of harvested fat emulsion and washing liquid is stratified in the conditioning chamber into a contaminant-lean fat fraction and a contaminant-rich remainder fraction. The fat fraction, which is substantially free of the remainder fraction, is recovered from the conditioning chamber as a desired product of the method.

20 Claims, 13 Drawing Sheets

Related U.S. Application Data application No. 15/154,890, filed on May 13, 2016, now Pat. No. 10,039,886.

(60) Provisional application No. 62/375,323, filed on Aug. 15, 2016.

(51) Int. Cl.

| | |
|---|---|
| *A61K 35/35* | (2015.01) |
| *A61M 5/31* | (2006.01) |
| *A61M 5/24* | (2006.01) |
| *A61M 5/315* | (2006.01) |
| *C12M 1/33* | (2006.01) |
| *C12N 5/077* | (2010.01) |
| *B01D 17/04* | (2006.01) |
| *A61M 1/00* | (2006.01) |
| *A61B 17/00* | (2006.01) |

(52) U.S. Cl.
CPC ........ *A61M 5/2448* (2013.01); *A61M 5/3145* (2013.01); *A61M 5/31513* (2013.01); *B01D 17/0208* (2013.01); *B01D 17/047* (2013.01); *C12M 45/02* (2013.01); *C12N 5/0653* (2013.01); *A61B 2017/00792* (2013.01); *A61M 1/0094* (2014.02); *A61M 2005/3104* (2013.01); *A61M 2005/3142* (2013.01); *A61M 2202/08* (2013.01)

(56) References Cited

U.S. PATENT DOCUMENTS

| | | | | |
|---|---|---|---|---|
| 5,002,538 A * | 3/1991 | Johnson | ............... | A61J 1/2096 604/240 |
| 5,052,999 A * | 10/1991 | Klein | ............... | A61M 1/0064 600/571 |
| 5,261,612 A * | 11/1993 | Ftaiha | ............... | A61L 27/24 241/199.12 |
| 5,352,410 A * | 10/1994 | Hansen | ............... | A61B 10/007 422/419 |
| 5,372,945 A * | 12/1994 | Alchas | ............... | A61F 2/062 422/421 |
| 5,603,845 A * | 2/1997 | Holm | ............... | B04B 1/02 210/782 |
| 5,741,428 A * | 4/1998 | Holm | ............... | B04B 1/02 210/749 |
| 5,744,360 A * | 4/1998 | Hu | ............... | A61F 2/062 435/325 |
| 5,804,366 A | 9/1998 | Hu | | |
| 6,020,196 A * | 2/2000 | Hu | ............... | A61M 1/00 435/283.1 |
| 6,316,247 B1 * | 11/2001 | Katz | ............... | A61L 27/3604 210/446 |
| 6,569,118 B2 * | 5/2003 | Johnson | ............... | A61M 5/347 604/164.04 |
| 7,585,670 B2 * | 9/2009 | Hedrick | ............... | A61K 35/28 435/325 |
| 7,887,795 B2 * | 2/2011 | Fraser | ............... | A61P 19/10 424/93.7 |
| 8,202,493 B2 * | 6/2012 | Buss | ............... | A61M 1/0084 210/406 |
| RE43,597 E * | 8/2012 | Johnson | ............... | A61M 5/347 604/164.04 |
| 8,414,778 B2 * | 4/2013 | Tajima | ............... | B01D 61/145 210/103 |
| 9,109,198 B2 * | 8/2015 | Khan | ............... | C12M 45/09 |
| 9,133,431 B2 * | 9/2015 | Peterson | ............... | C12N 5/0653 |
| 9,333,447 B2 * | 5/2016 | McKay | ............... | B01D 33/0158 |
| 9,480,464 B2 * | 11/2016 | Levine | ............... | A61B 10/0283 |
| 9,549,753 B2 * | 1/2017 | Gordon | ............... | A61B 17/3203 |
| 9,695,398 B2 | 7/2017 | Peterson et al. | | |
| 10,039,886 B2 * | 8/2018 | Pilkington | ......... | A61M 5/31511 |
| 10,092,600 B2 * | 10/2018 | Huang | ............... | A61L 27/3604 |
| 10,125,345 B2 * | 11/2018 | Nash | ............... | C12M 47/04 |
| 10,183,101 B2 * | 1/2019 | Conlan | ............... | A61M 37/0015 |
| 10,188,777 B2 * | 1/2019 | Conlan | ............... | A61M 37/0015 |
| 10,279,325 B1 * | 5/2019 | Crombie | ............... | B01F 5/0685 |
| 2002/0010433 A1 * | 1/2002 | Johnson | ............... | A61M 5/347 604/241 |
| 2005/0084961 A1 * | 4/2005 | Hedrick | ............... | A61K 35/28 435/366 |
| 2007/0100277 A1 * | 5/2007 | Shippert | ............... | A61M 1/0064 604/27 |
| 2007/0225686 A1 * | 9/2007 | Shippert | ............... | A61M 1/0001 604/542 |
| 2008/0154240 A1 * | 6/2008 | Shippert | ............... | A61M 1/0001 604/542 |
| 2009/0239299 A1 * | 9/2009 | Buss | ............... | A61M 1/0084 435/374 |
| 2010/0279405 A1 * | 11/2010 | Peterson | ............... | C12M 47/04 435/366 |
| 2015/0218506 A1 * | 8/2015 | Nash | ............... | C12M 47/04 435/379 |
| 2015/0352266 A1 * | 12/2015 | Gourlay | ............... | A61M 1/0001 604/542 |
| 2015/0374888 A1 * | 12/2015 | Shippert | ............... | A61M 1/0001 604/542 |
| 2016/0106889 A1 * | 4/2016 | Conlan | ............... | A61M 1/0056 604/319 |
| 2016/0333305 A1 * | 11/2016 | Pilkington | ............... | A61M 1/0094 |
| 2016/0367757 A1 * | 12/2016 | Pilkington | ............... | A61M 5/31511 |
| 2017/0049942 A1 * | 2/2017 | Conlan | ............... | A61M 37/0015 |
| 2017/0203040 A1 * | 7/2017 | Conlan | ............... | A61M 37/0015 |
| 2017/0368226 A1 * | 12/2017 | Pilkington | ............... | B01D 17/047 |
| 2018/0207331 A1 * | 7/2018 | Conlan | ............... | A61M 1/0005 |
| 2018/0230418 A1 * | 8/2018 | Nash | ............... | C12M 47/04 |
| 2018/0280623 A1 * | 10/2018 | Pilkington | ............... | A61M 5/31513 |
| 2019/0046231 A1 * | 2/2019 | Conlan | ............... | A61M 1/0056 |
| 2019/0143005 A1 * | 5/2019 | Conlan | ............... | A61M 37/0015 604/542 |

OTHER PUBLICATIONS

Tulip Product Catalog, select pages, Jan. 2014.
Alexander, Robert W., "Understanding Mechanical Emulsification vs. Enzymatic Isolation of tSVF From Adipose Tissue", Journal of Prolotherapy, 8:e947-e960, Feb. 2016.
Tonnard, Patrick, et al., "Nanofat Grafting: Basic Research and Clinical Applications", Plastic and Reconstructive Surgery Journal, v. 132(4), at pp. 1017-1026, Oct. 2013.

* cited by examiner

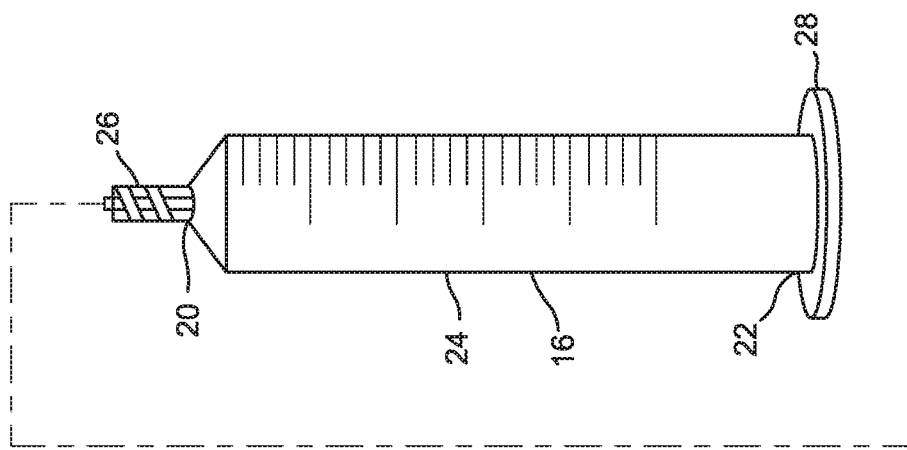
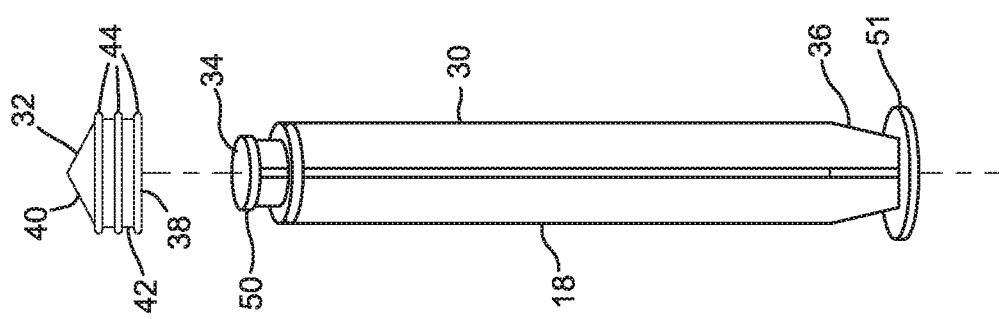
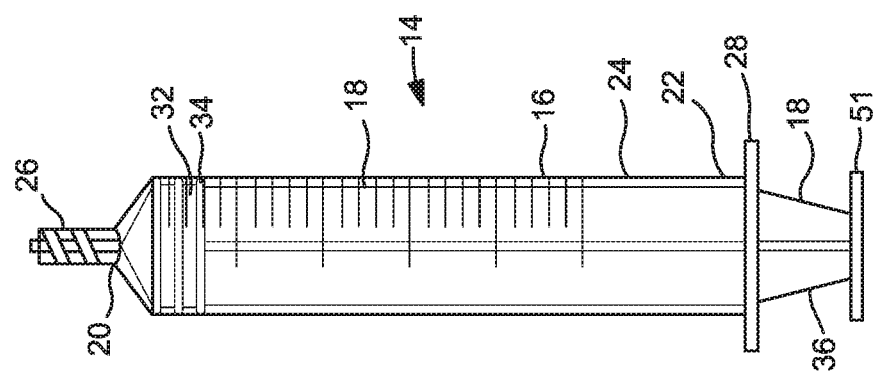

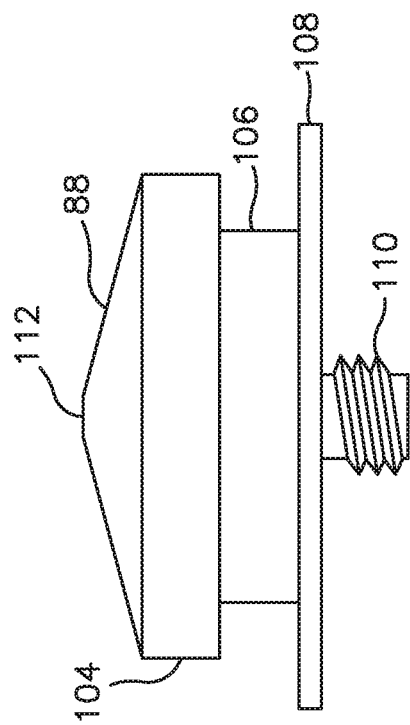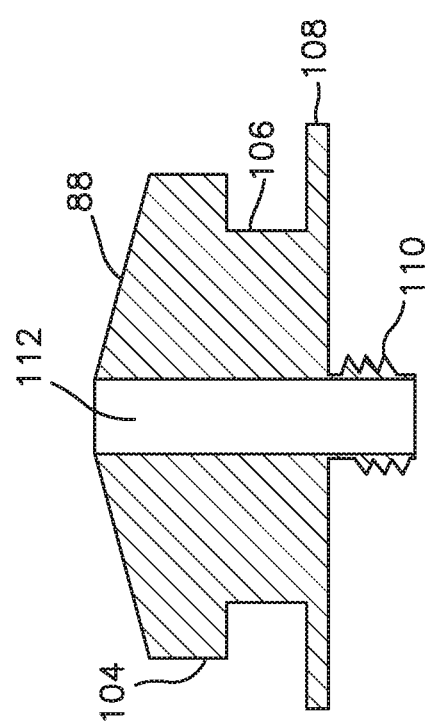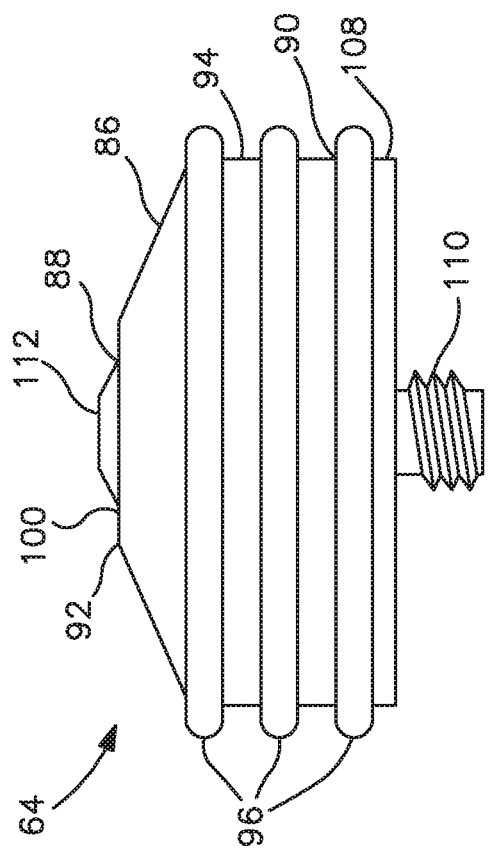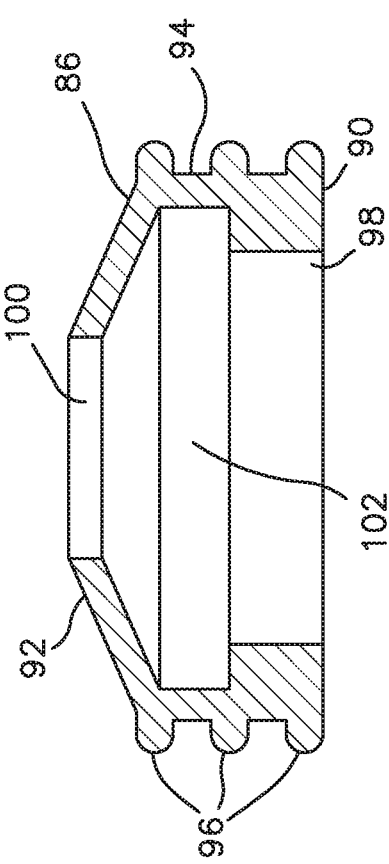

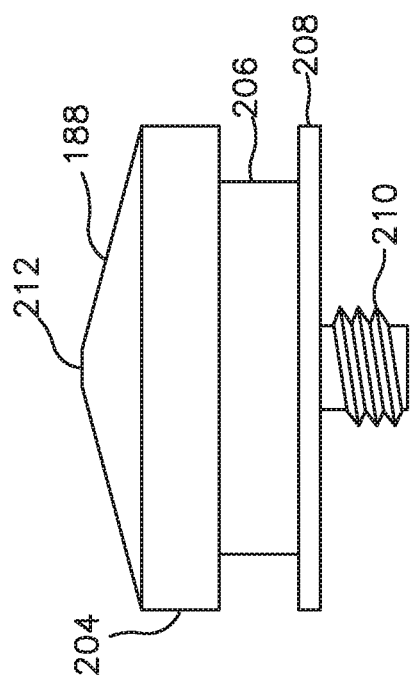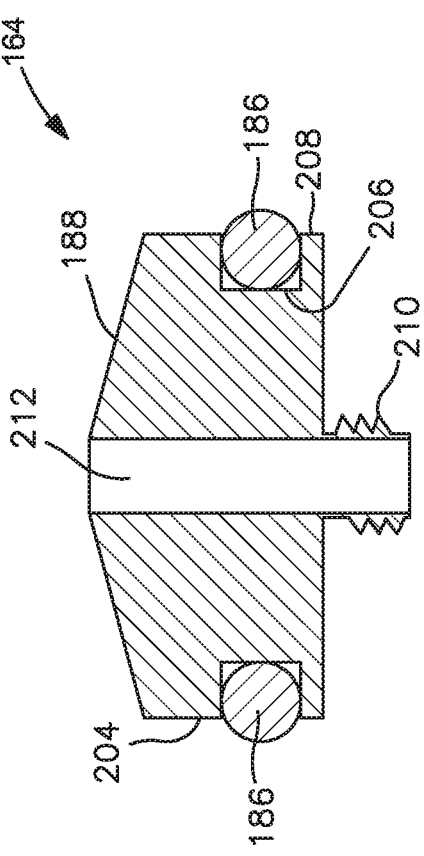

CONDITIONING HARVESTED FAT FOR RE-INJECTION

RELATED APPLICATIONS

This is a non-provisional patent application claiming the priority of Provisional Patent Application Ser. No. 62/375,323, which is filed on Aug. 15, 2016 and which is incorporated herein by reference. This is also a continuation-in-part patent application claiming the priority of patent application Ser. No. 15/154,885 and patent application Ser. No. 15/154,890, which are both filed on May 13, 2016 and both of which are incorporated herein by reference. Patent application Ser. Nos. 15/154,885 and 15/154,890 are both non-provisional patent applications claiming the priority of Provisional Patent Application Serial Nos. 62/162,367 and 62/162,389, which are both filed on May 15, 2015 and both of which are incorporated herein by reference. Patent application Ser. No. 15/154,890 is also a continuation-in-part patent application claiming the priority of patent application Ser. No. 14/846,357, which is filed on Sep. 4, 2015 and which is incorporated herein by reference. Patent application Ser. No. 14/846,357 is a non-provisional patent application claiming the priority of Provisional Patent Application Ser. No. 60/045,926, which is filed on Sep. 4, 2014 and which is incorporated herein by reference.

BACKGROUND OF THE INVENTION

The present invention relates generally to medical devices and methods and more particularly to devices and methods having utility in clinical applications for fat transfer.

Fat transfer, alternately termed fat grafting, comprises two or more procedures or sub-processes performed in series. Fat transfer processes are typically initiated with a fat harvesting procedure and are concluded with a fat re-injection procedure. The fat harvesting procedure and fat re-injection procedure are commonly performed on the same patient. In such cases, the fat transfer process is termed an autologous process.

Fat harvesting entails removing a harvested fat emulsion from the hypodermis of a patient. The hypodermis is the subdermal or subcutaneous innermost layer of the skin which is one of the primary sites on the body where fat is produced and stored. The harvested fat emulsion is characterized at least in part as native adipose material which appears as an amalgam of loose connective tissue and fat lobules. On a microscopic level, the native adipose material is characterized as an adipose tissue complex which is a diverse heterogeneous mixture including inter alia adipocytes, precursor adipocytes, stromal cells, stem cells, macrophages, free lipids dissociated from ruptured adipocytes, perivascular matrix, extracellular matrix and native scaffolding. Preferred harvesting sites on the body include the fatty lower layer of skin on the thighs or stomach of the patient. Fat harvesting is performed in accordance with any number of well-known techniques including liposuction or lipoplasty.

Fat re-injection entails injecting a re-injection material into an injection site that is different from the harvesting site. In the case of an autologous fat transfer process, the injection site is on the same body as the harvesting site, but is at a different location on the patient's body. The re-injection material is generally characterized as a fat-containing material. The preferred location of the injection site on the body depends on the particular clinical application for the fat transfer process. For example, potential injection sites in cosmetic applications for fat transfer include the skin of the face, breasts, cheeks, lips, buttocks, and/or chin. The re-injection material acts as a superficial filler in cosmetic applications to desirably increase volume at the injection site and enhance the appearance of the patient. Alternate injection sites may be selected for other clinical fat transfer applications, such as for skin anti-aging, hair regeneration, restoration of sun/radiation damaged skin, restoration of abnormally scarred skin, healing of chronic flesh wounds and treatment of many musculoskeletal disorders.

There are a number of intervening procedures that may be performed after the fat harvesting procedure and before the fat re-injection procedure, which are termed fat conditioning procedures. Fat conditioning procedures are designed to enhance the suitability of the re-injection material for use in the fat re-injection procedure. Many fat conditioning procedures are performed in serial combination with other fat conditioning procedures. One general type of fat conditioning procedure is termed fat decontamination. Fat decontamination procedures are designed in general to remove undesirable non-fat materials, termed contaminants, from the harvested fat emulsion before fat re-injection. Common contaminants in the harvested fat emulsion include such non-fat liquids as blood and tumescent fluid which are desirably excluded from the ultimate re-injection material.

A specific type of fat decontamination procedure is termed fat washing. Fat washing procedures are preferably performed on the harvested fat emulsion before any other intervening fat conditioning procedures and are frequently performed immediately after the harvested fat emulsion has been withdrawn from the body via the fat harvesting procedure. The fat washing procedure is initiated by fully mixing a volume of an aqueous washing liquid with the harvested fat emulsion. The resulting mixture of the harvested fat emulsion and aqueous washing liquid stratifies relatively rapidly into at least two layers. One layer is termed a contaminant-rich layer and another layer is termed a contaminant-lean layer. The contaminant-rich layer is characterized as having a significantly higher concentration of contaminants and aqueous washing liquid and a significantly lower concentration of fat than the contaminant-lean layer, whereas the contaminant-lean layer is characterized as having a significantly higher concentration of fat and a significantly lower concentration of contaminants and aqueous washing liquid than the contaminant-rich layer. The contaminant-lean and contaminant-rich layers are readily separable from one another by gravity. The resulting contaminant-lean layer, which is isolated from the contaminant-rich layer, is suitable for further fat conditioning before fat re-injection or may be suitable as is for use as the re-injection material in a fat re-injection procedure.

Another fat conditioning procedure is termed fat compounding. Fat compounding procedures enhance the composition of the re-injection material via the addition of certain desirable non-fat liquids, such as platelet rich plasma (PRP), to the re-injection material recovered from the harvested fat emulsion. Yet another common fat conditioning procedure is termed fat sizing. A harvested fat emulsion by its nature contains fat particles in a broad range of particle sizes upon its removal from the body. These fat particles may be classified in different particle size categories listed as follows from largest to smallest: macrofat, microfat, millifat and nanofat. The object of fat sizing procedures is to increase the fraction of nanofat in the re-injection material used in the ultimate fat re-injection procedure. An exemplary fat re-injection procedure using a re-injection material having a high concentration of nanofat is described in "Nanofat Grafting: Basic Research and Clinical Applications," Tonnard, Patrick, et al., *Plastic and Reconstructive Surgery Journal*, v. 132(4), at pp. 1017-26, October 2013, which is incorporated herein by reference.

Nanofat is particularly suited for re-injection because it readily flows through very sharp, fine cannulas having a size range of about 27 to 30 gauge. Practitioners prefer to use these fine cannulas in fat re-injection procedures because they are less invasive and disruptive to the patient and can substantially reduce pain, bruising and/or other undesirable side effects of the fat re-injection procedure while simultaneously shortening patient recovery time. Fine cannulas also advantageously enable more precise placement of the re-injection material in the injection site, particularly with respect to intradermal and small joint placements, which are very challenging therapeutic sites. Nanofat advantageously does not substantially clog or otherwise impede flow through fine cannulas as compared to larger fat particle sizes which frequently clog them.

It is also believed that there may be substantial therapeutic advantages attributable to the use of nanofat versus larger fat particle sizes, particularly with respect to certain specific clinical fat transfer applications. For example, nanofat has been found to enhance the therapeutic efficacy of cosmetic applications for fat transfer by producing markedly better results in the ultimate appearance of the patient, particularly in the treatment of superficial dermal layers such as eyelids and the like, when compared to patients treated with larger particle-size fats. The reason for these therapeutic advantages is not fully understood, but it is believed that the therapeutic advantages result from factors in addition to, or other than, the small particle size of the nanofat. One theory is that there is a substantially greater residual presence of therapeutically beneficial adipose and non-adipose materials, some or all of which may be bioactive, that are coincidentally retained in the nanofat when it is isolated from the remainder of the harvested fat emulsion in preparation for re-injection and that the presence of these materials enhances the efficacy of the clinical fat transfer application. This theory is discussed in "Understanding Mechanical Emulsification (Nanofat) Versus Enzymatic Isolation of Tissue Stromal Vascular Fraction (tSVF) Cells from Adipose Tissue: Potential Uses in Biocellular Regenerative Medicine," Alexander M. D., Robert W., *Journal of Prolotherapy*, v. 8:2016, at pp. e947-e960, Mar. 11, 2016, which is incorporated herein by reference. The adipose-derived tissue stromal vascular fraction of cells (AD-tSVF) is a highly desirable fraction of the adipose tissue complex for re-injection because it includes stromal cells and bioactive scaffolding.

Given the above-recited advantages attributable to the use of nanofat in fat re-injection procedures, fat sizing procedures that separate and recover the nanofat from the bulk harvested fat emulsion obtained in fat harvesting procedures are highly desirable. The recovered nanofat is the primary component of the re-injection material in the fat re-injection procedure, while the remainder of the harvested fat emulsion is excluded from the re-injection material or at least reduced in amount. Fat sizing procedures also desirably increase the volume and/or density of the nanofat in the ultimate re-injection material by breaking down the particle size of the fat in the harvested fat emulsion.

Additional fat conditioning procedures include centrifugation, filtration and decantation. In known centrifugation procedures, the harvested fat emulsion is rotated in a centrifuge container at high speed. The centrifugal force that the centrifuge applies to the harvested fat emulsion typically stratifies it into three discrete vertical layers of different density. The bottom centrifugation layer contains the most dense material, termed the pellet, and settles to the bottom of the centrifuge container. The top centrifugation layer contains the least dense material and rises to the top of the centrifuge container. The middle centrifugation layer contains an intermediate density material and resides between the top and bottom centrifugation layers in the centrifuge container. The majority of the nanofat has been found to reside in the middle centrifugation layer which the practitioner recovers as the re-injection material for re-injection into the body to the exclusion of the other centrifugation layers. An example of a specific centrifugation procedure is disclosed in our co-pending U.S. patent application Ser. No. 15/154,890 filed on May 13, 2016 and incorporated herein by reference.

In known filtration procedures, the harvested fat emulsion is applied to a filtration medium which permits nanofat to pass through it in the filtrate while trapping the unwanted remainder of the harvested fat emulsion on the filtration medium as a filter cake. An example of a specific filtration procedure is disclosed in our co-pending U.S. patent application Ser. No. 15/154,885 filed on May 13, 2016 and incorporated herein by reference.

In known decantation procedures, gravity acts on the harvested fat emulsion while it rests in a decanter for an extended period of time, e.g., several minutes or more. The force of gravity, like centrifugal force, causes the harvested fat emulsion to separate into multiple discrete layers of different density. The practitioner retrieves the nanofat layer, i.e., the layer containing the majority of the nanofat, as the re-injection material for re-injection into the body to the exclusion of the other layer(s) by simply pouring off each layer into separate containers.

A need is recognized herein for a fat conditioning apparatus having utility in any one of a plurality of procedures that efficiently and effectively produce a satisfactory re-injection material from a harvested fat emulsion for re-injection into the body of a patient. Accordingly, it is an object of the present invention to provide an apparatus that satisfies the above need. It is further an object of the present invention to provide one or more methods that satisfy the above need. These objects and others are accomplished in accordance with the invention described hereafter.

SUMMARY OF THE INVENTION

The present invention may be characterized as a fat conditioning apparatus. An embodiment of the fat conditioning apparatus includes a conditioning vessel. The conditioning vessel comprises an end and sidewall that are fixed relative to one another. The conditioning vessel further comprise a plug that is displacable relative to the end and sidewall. The end and plug are displacably positioned opposite one another and the sidewall extends between them. The interior of the conditioning vessel defines a conditioning reservoir that is bounded by the end, sidewall and plug. The end has a port formed therethrough that is selectively blocked or unblocked by a selectively removable connection member cap manually positioned across the port or removed from the port by the user. The conditioning vessel further comprises a filter element positioned in the conditioning chamber between the end and plug across the conditioning chamber cross-section. The filter element is preferably fixed relative to the end and sidewall and is preferably positioned immediately adjacent to the end and more preferably still, in substantial engagement with the end. As such any material exiting the conditioning chamber via the port when the user has selectively unblocked the port by removing the connection member cap must pass through the filter element. An alternate embodiment of the present fat conditioning apparatus includes the above-recited conditioning vessel and one or more transfer syringes.

A preferred function of the filter element within the fat conditioning apparatus is to remove an over-size fraction, such as solids or semi-solids, from any material, such as a harvested fat emulsion, passing through the filter element. Alternate or complementary functions of the filter element may include reducing the particle size of fat in a harvested fat emulsion passing through the filter element to increase the nanofat fraction of the harvested fat emulsion in the manner of a fat sizing procedure and/or to effect complete mixing of a harvested fat emulsion and an additive material to form a homogeneous compounded fat emulsion in the manner of a fat compounding procedure.

The present invention may be alternately characterized as a fat conditioning method. In accordance with an embodiment of the fat conditioning method, the fat conditioning method is more particularly a fat washing method, wherein a harvested fat emulsion and a washing liquid are injected into a conditioning chamber of a conditioning vessel. The conditioning chamber is bounded by a displacable plug and has a variable volume. The plug is displaced in an outward expansion direction within the conditioning vessel in response to injection of the harvested fat emulsion and washing liquid into the conditioning chamber, thereby expanding the variable volume of the conditioning chamber. The harvested fat emulsion and washing liquid are mixed in the conditioning chamber to produce a mixture thereof. The mixture is stratified in the conditioning chamber into a contaminant-lean fat fraction and a contaminant-rich remainder fraction. The fat fraction is recovered from the conditioning chamber to the substantial exclusion of the remainder fraction.

Another embodiment of the fat conditioning method includes a first injection step, a first displacement step, a second injection step, a second displacement step, a mixing step, a stratification step and a recovery step. In the first injection step, a harvested fat emulsion is injected into a conditioning chamber of a conditioning vessel. The conditioning chamber has a variable volume and is fixably bounded on a first conditioning chamber end by a fixed end of the conditioning vessel and is variably bounded on a second conditioning chamber end by a plug displacable within the conditioning vessel. The harvested fat emulsion may be injected into the conditioning chamber through the plug from a transfer syringe engaging the plug. The fixed end of the conditioning vessel may have a port formed therein and the harvested fat emulsion is injected into the conditioning chamber while the port is blocked to prevent fluid passage therethrough. In the first displacement step, the plug is displaced in an outward expansion direction within the conditioning vessel in response to injection of the harvested fat emulsion into the conditioning chamber, thereby expanding the variable volume of the conditioning chamber. In the second injection step, a washing liquid is injected into the conditioning chamber. The washing liquid may be injected into the conditioning chamber through the plug from a transfer syringe engaging the plug. The washing liquid may be injected into the conditioning chamber while the port formed in the fixed end of the conditioning vessel is blocked to prevent fluid passage therethrough. In the second displacement step, the plug is displaced in the outward expansion direction within the conditioning vessel in response to injection of the washing liquid into the conditioning chamber, thereby expanding the variable volume of the conditioning chamber. In the mixing step, the harvested fat emulsion and the washing liquid are mixed in the conditioning chamber to produce a mixture of the harvested fat emulsion and the washing liquid. The mixing of the harvested fat emulsion and the washing liquid in the conditioning chamber may be facilitated by agitation of the harvested fat emulsion and the washing liquid in the conditioning chamber. In the stratification step, the mixture is stratified into a contaminant-lean fat fraction and a contaminant-rich, wash liquid-rich remainder fraction. In the recovery step, the fat fraction substantially free of the remainder fraction is recovered from the conditioning chamber.

In accordance with the present embodiment, the method may further comprise removing the remainder fraction from the conditioning chamber before recovering the fat fraction. The remainder fraction may be removed from the conditioning chamber by unblocking the port formed therein to permit fluid passage therethrough and discharging the remainder fraction from the conditioning chamber via the port. The method may further comprise passing the remainder fraction through a filter element positioned in the conditioning chamber upstream of the first conditioning chamber end. The remainder fraction may be passed through the filter element while the port is unblocked and the filter element is positioned in the conditioning chamber upstream of the port. The fat fraction may be recovered from the conditioning chamber through the plug into a transfer syringe engaging the plug.

Yet another alternate embodiment of the fat conditioning method includes a first injection step, a first displacement step, a second injection step, a second displacement step, a mixing step, a stratification step, a filtration step, a removal step and a recovery step. In the first injection step, a harvested fat emulsion is injected into a conditioning chamber of a conditioning vessel through a plug displacable within the conditioning vessel from a transfer syringe engaging the plug. The conditioning chamber has a variable volume and is bounded on a first conditioning chamber end by a fixed end of the conditioning vessel having a port formed therein and is variably bounded on a second conditioning chamber end by the plug. The harvested fat emulsion is injected into the conditioning chamber while the port is blocked to prevent fluid passage therethrough. In the first displacement step, the plug is displaced in an outward expansion direction within the conditioning vessel in response to injection of the harvested fat emulsion into the conditioning chamber, thereby expanding the variable volume of the conditioning chamber. In the second injection step, injecting a washing liquid is injected into the conditioning chamber through the plug from the transfer syringe or an other transfer syringe engaging the plug, wherein the washing liquid is injected into the conditioning chamber while the port is blocked to prevent fluid passage therethrough. In the second displacement step, the plug is displaced in the outward expansion direction within the conditioning vessel in response to injection of the washing liquid into the conditioning chamber, thereby expanding the variable volume of the conditioning chamber. In the mixing step, the harvested fat emulsion and the washing liquid are mixed in the conditioning chamber to produce a mixture of the harvested fat emulsion and the washing liquid. In the stratification step, the mixture is stratified into a contaminant-lean fat fraction and a contaminant-rich, wash liquid-rich remainder fraction. In the filtration step, the remainder fraction is passed through a filter element positioned in the conditioning chamber upstream of the port while the port is unblocked. In the removal step, the remainder fraction is removed from the conditioning chamber via the port. In the recovery step, the fat fraction is recovered substantially free of the remainder fraction from the conditioning chamber by drawing the fat fraction through the plug into the transfer syringe or the other transfer syringe engaging the plug.

The injection and displacement steps have been recited in certain of the above embodiments as paired sequences of first and second steps. It is understood that the labeling of these steps as first and second steps and/or the order in which these steps are recited above is merely for purposes of illustration and not by way of limitation. The recitation of first and second steps in the above embodiments is intended to encompass both the case where the first injection and displacement steps are performed first followed by performance of the second injection and displacement steps and the case where the second injection and displacement steps are performed first followed by performance of the first injection and displacement steps.

The invention will be further understood from the drawings and the following detailed description.

BRIEF DESCRIPTION OF THE SEVERAL VIEWS OF THE DRAWINGS

The below-listed drawing figures illustrate one or more embodiments of the present invention by way of example and not by way of limitation. Common reference characters may be used among the different drawing figures to indicate the same or similar structural elements.

FIG. 2 is an elevation view of a transfer syringe having utility in the fat conditioning apparatus of FIG. 1.

FIG. 3 is an exploded view of the transfer syringe of FIG. 2.

FIG. 4 is a section view of the plunger stopper shown in FIGS. 2 and 3.

FIG. 8 is an elevation view of the plug shown in FIG. 6.

FIG. 9 is a section view of the plug cap shown in FIG. 8.

FIG. 10 is an elevation view of the plug body shown in FIG. 8.

FIG. 11 is a section view of the plug body shown in FIG. 8.

FIG. 12 is a section view an alternate embodiment of a plug that has utility in the conditioning vessel shown in FIG. 5.

FIG. 13 is an elevation view of a plug body included in the plug shown in FIG. 12.

DETAILED DESCRIPTION OF THE INVENTION

Figure 1:
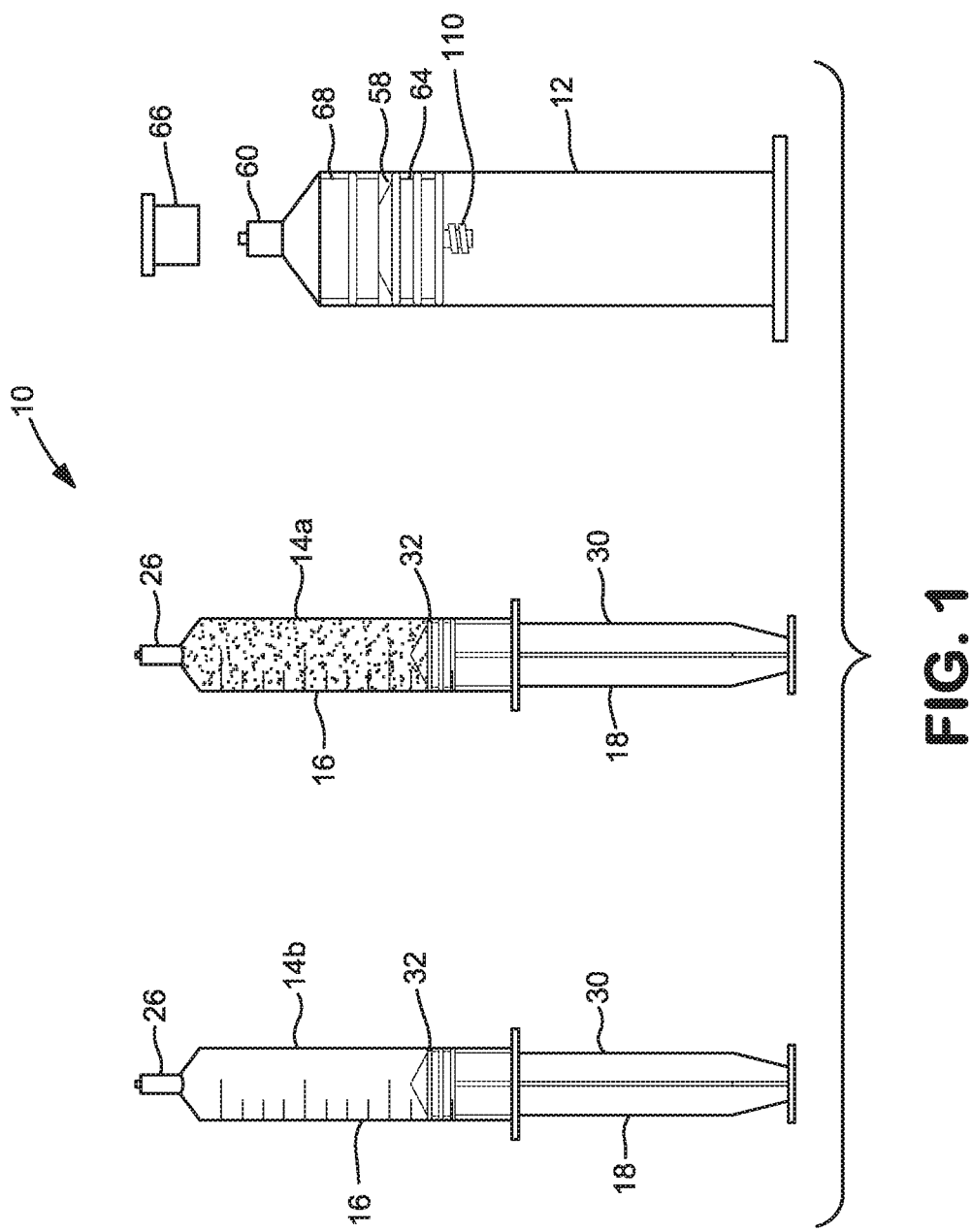
FIG. 1 shows an embodiment of a fat conditioning apparatus.

One embodiment of a fat conditioning apparatus generally comprises a conditioning vessel. An alternate embodiment of a fat conditioning apparatus generally comprises a conditioning vessel and one or more transfer syringes. The specific number of transfer syringes provided in accordance with the present embodiment is within the purview of one of ordinary skill in the art depending on the particular needs of the specific application for which the apparatus is employed. As such, the present embodiment is not limited to any specific number of transfer syringes. An alternate more specific embodiment of a fat conditioning apparatus is shown herein by way of example with reference to FIG. 1 and generally designated 10. The fat conditioning apparatus 10 of the present exemplary specific embodiment has a conditioning vessel 12 and two transfer syringes 14a, 14b.

Regardless of their number, each transfer syringe provided in each of the latter two embodiments recited above of the fat conditioning apparatus preferably has a similar construction. A representative transfer syringe is described hereafter with reference to FIGS. 2 and 3 and is generally designated 14. It is understood that this description can apply equally to each and every transfer syringe employed in the fat conditioning apparatus and specifically applies to the transfer syringes 14a, 14b of the present embodiment. The transfer syringe 14 is preferably an off-the-shelf, sterile, disposable, single-use syringe which includes a barrel 16 and a plunger 18. The barrel 16 is preferably an elongate hollowed-out cylinder formed in its entirety from a disposable transparent or translucent rigid plastic. The barrel 16 has a first end 20, an opposite second end 22 and an open interior which is bounded by a continuous tubular sidewall 24. The open interior of the barrel 16 defines a fluid retention chamber with a variable volume which is selectively adjustable in a manner described hereafter.

A connection member 26 is integrally formed with the first end 20 of the barrel 16. The connection member 26 is preferably a Luer coupler. A Luer coupler is a conventional connector fitting known for a multitude of medical applications. The present Luer coupler 26 has either a male or female configuration and mates with a Luer coupler of the opposite configuration associated with another fluid-containing chamber to provide a fluid-tight (i.e., non-leaking) coupling between the two chambers, wherein each of the Luer couplers functions as a fluid port for its respective chamber, thereby enabling fluid communication between the two chambers when the Luer couplers are mated together. When not mated with a Luer coupler of another fluid-containing chamber, the present Luer coupler 26 provides fluid communication between the fluid retention chamber in the interior of the barrel 16 and the external environment exterior to the barrel 16 via the Luer coupler 26. The second end 22 of the barrel 16 is substantially open across the entire diameter of the interior. A barrel finger hold 28 is integrally formed with, and extends outwardly from, the outside edge of the second end 22 of the barrel 16. The barrel finger hold 28 facilitates gripping the second end 22 of the barrel 16 during operation of the fat conditioning apparatus 10 in a manner described hereafter.

The plunger 18 is an elongate structure which includes a plunger body 30 and a plunger stopper 32 that is removably attachable to the plunger body 30. The plunger 18 has a first end 34 and an opposite a second end 36. The plunger body 30 is a unitary structure having an elongate shape and is preferably formed in its entirety from a disposable rigid plastic. The plunger stopper 32 is a unitary structure having a squat cylindrical shape and is preferably formed from an at least somewhat compressible, deformable elastic material such as rubber, synthetic rubber or other like elastomeric material. The plunger stopper 32 is removably attached to the plunger body 30 at the first end 34 of the plunger 18.

In accordance with a preferred embodiment described with specific reference to FIG. 4 and continuing reference to FIGS. 2 and 3, the plunger stopper 32 has an open end 38, a closed end 40, an outer sidewall 42 extending perpendicularly between the open and closed ends 38, 40 and a plurality of spaced-apart, compressible, deformable circumferential ribs 44 extending outwardly from the outer sidewall 42. The open end 38 of the plunger stopper 32 has a retention lip 46 extending around its circumferential edge. The closed end 40, outer sidewall 42 and retention lip 46 in combination define an interior cavity of the plunger stopper 32, termed a plunger retention chamber 48. The plunger stopper 32 is removably mounted on the first end 34 of the plunger 18 by positioning the open end 38 of the plunger stopper 32 over a stopper coupler 50 integral with a first end of the plunger body 30 that corresponds to the first end 34 of the plunger 18. The plunger stopper 32 is press fitted onto the stopper coupler 50 causing the retention lip 46 to deform around the stopper coupler 50, thereby enabling the stopper coupler 50 to slip past the retention lip 46 into the plunger retention chamber 48. The retention lip 46 retains the stopper coupler 50 in the plunger retention chamber 48 so that the plunger stopper 32 substantially encloses the stopper coupler 50 and is integral with the first end 34 of the plunger 18.

The first end 34 of the plunger 18 is termed an inner end because it is received in the open second end 22 of the barrel 16 of the assembled syringe 14 and extends into the interior of the barrel 16. The diameter of the outer sidewall 42 of the plunger stopper 32 and the width of the plunger body 30 are each preferably about equal to the inside diameter of the barrel 16. In the present case "about equal to" means that the diameter of the outer sidewall 42 of the plunger stopper 32 and the width of the plunger body 30 are preferably only very slightly smaller than the diameter of the interior of the barrel 16. In contrast, the outside diameters of the compressible ribs 44 of the plunger stopper 32 are preferably slightly greater than the diameter of the interior of the barrel 16 when the ribs 44 are uncompressed. The slightly oversize fit of the ribs 44 relative to the interior of the barrel 16 deforms and compresses the ribs 44 against the sidewall 24 of the barrel 16. Nevertheless, the material of the plunger stopper 32 exhibits sufficient structural integrity that the ribs 44 provide a reliably secure fluid tight seal between the outside edge of the plunger stopper 32 and the sidewall 24 of the barrel 16. Accordingly, the plunger 18 nests snugly within the interior of the barrel 16 without fluid leakage past the plunger stopper 32, but is still slidably displacable therein relative to the barrel 16 when a manual pushing or pulling force is applied to the plunger 18.

The plunger 18 preferably has a length greater than the length of the interior of the barrel 16 so that the second end 36 of the plunger 18, termed the outer end, extends out of the open second end 22 of the barrel 16 when the plunger 18 is fully depressed into the interior of the barrel 16 with the plunger stopper 32 abutting the first end 20 of the barrel 16. A plunger finger hold 51 is integrally formed with, and extends outwardly from, the plunger body 30 at the second end 36 of the plunger 18. The plunger finger hold 51 facilitates gripping the second end 36 of the plunger 18 during operation of the fat conditioning apparatus 10. Thus, manually pulling on the plunger 18, more particularly on the second end 36 of the plunger 18, and more particularly still on the plunger finger hold 51, displaces the plunger 18 in an outward expansion direction away from the first end 20 of the barrel 16. Manually pushing on the plunger 18, more particularly on the second end 36 of the plunger 18, and more particularly still on the plunger finger hold 51, displaces the plunger 18 in an opposite inward contraction direction toward the first end 20 of the barrel 16.

The plunger 18 acts in the manner of a piston slidably positioned within a variable-volume fluid retention chamber formed in the interior of the barrel 16 between the first end 20 of the barrel 16 and the plunger stopper 32. The variable-volume fluid retention chamber increases in volume as the degree of displacement in the outward expansion direction increases. Thus, manually pulling on the plunger 18 enables the user to draw fluid into the barrel 16 of the transfer syringe 14. The variable-volume fluid retention chamber decreases in volume as the degree of displacement in the inward contraction direction increases. Thus, depressing, i.e., pushing on, the plunger 16 enables the user to evacuate fluid from the barrel 16 of the transfer syringe 14.

Figure 5:
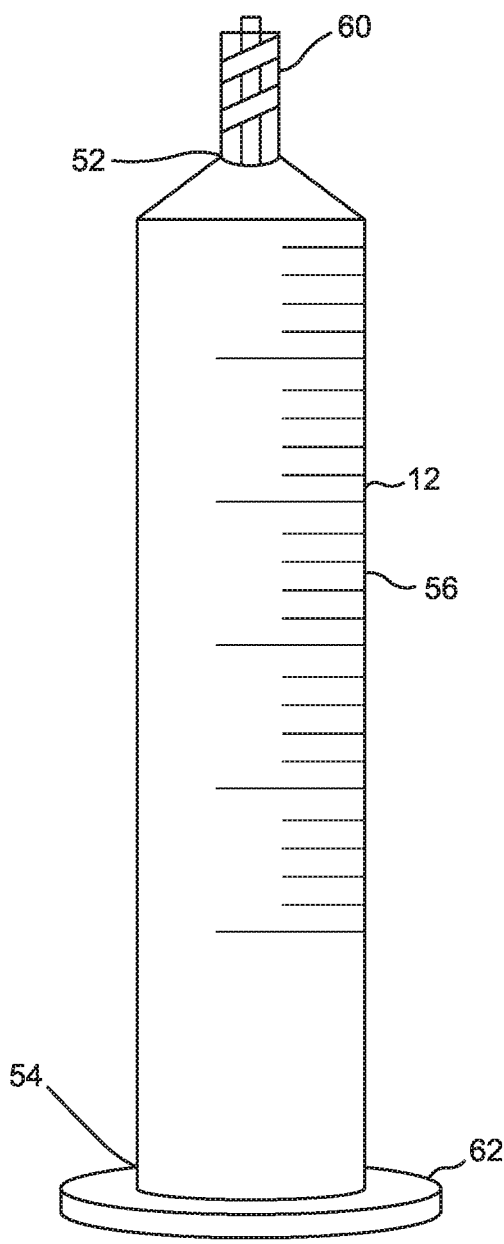
FIG. 5 is an elevation view of a conditioning vessel having utility in the fat conditioning apparatus of FIG. 1, wherein the internal components of the conditioning vessel are excluded from the instant view.
Figure 6:
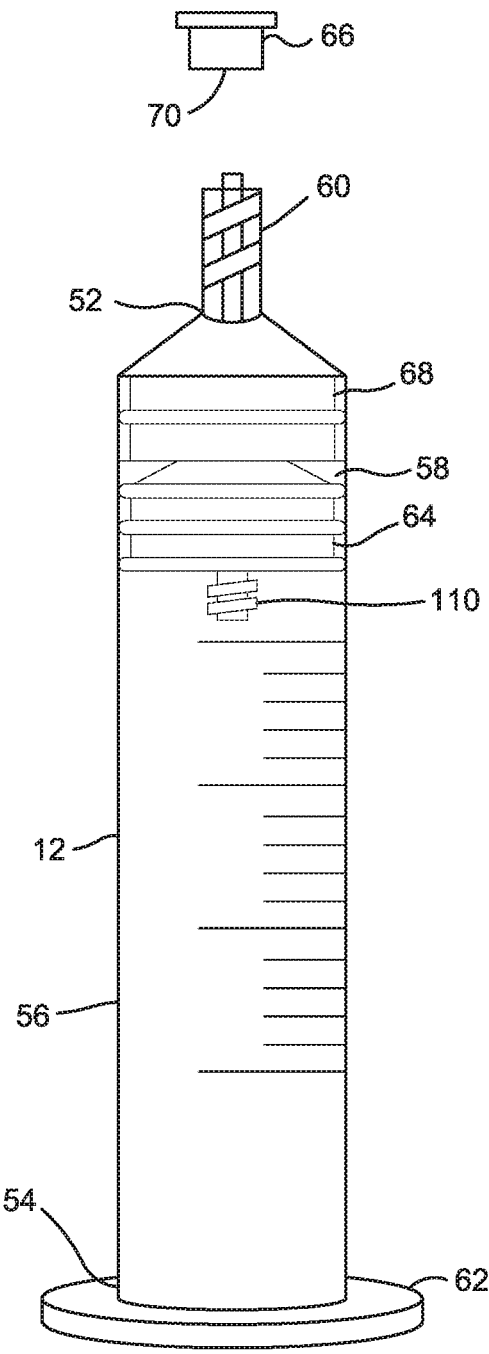
FIG. 6 is an elevation view of the conditioning vessel of FIG. 5 including its internal elements. For clarity, the instant view omits some of the volume markings on the conditioning vessel that are shown in FIG. 5.

In accordance with a preferred embodiment described with reference to FIGS. 5 and 6, the conditioning vessel 12 has a substantially similar construction to the barrel 16 of the transfer syringe 14 shown in FIG. 3. As such, a preferred conditioning vessel 12 is an elongate hollowed-out cylinder formed in its entirety from a disposable transparent or translucent rigid plastic. The conditioning vessel 12 has a closed circular first end 52, an opposite open circular second end 54 and an open interior which is bounded by a continuous tubular sidewall 56 extending perpendicularly between the first and second ends 52, 54. The open interior of the conditioning vessel 12 defines a cylindrical conditioning chamber 58 (shown in FIGS. 15-20) having a selectively adjustable volume. A connection member 60 is integrally formed with the first end 52 of the conditioning vessel 12. The connection member 60 is preferably a Luer coupler that provides selective fluid communication between the conditioning chamber 58 and the exterior of the conditioning chamber 58. As such, the first end 52 of the conditioning vessel 12 and integrally formed Luer coupler 60 define a fixed boundary of a first end of the conditioning chamber 58. The Luer coupler 60 functions as a selectively blocked or unblocked port through the first end 52 of the conditioning vessel 12 through which fluid or other materials can enter or exit the conditioning chamber 58 and correspondingly the conditioning vessel 12 when the port is unblocked. The second end 54 of the conditioning vessel 12 is substantially open across the entire diameter of the conditioning vessel 12. A vessel finger hold 62 is integrally formed with, and extends outwardly from, the outside edge of the second end 54 of the conditioning vessel 12. The vessel finger hold 62 facilitates gripping the second end 54 of the conditioning vessel 12 during operation of the fat conditioning apparatus 10.

The selectively adjustable volume of the conditioning chamber 58 is enabled by a slidably displacable plug 64 that defines a variable boundary of a second end of the conditioning chamber 58 which is opposite the second end of the conditioning chamber 58 that is fixably bounded by the the first end 52 of the conditioning vessel 12 and integrally formed Luer coupler 60. The plug 64 is among several fittings for the conditioning vessel 12 described hereafter. Additional fittings for the conditioning vessel 12 include a selectively removable connection member cap 66 and a fixed filter cartridge 68. The connection member cap 66 is sized and configured to selectively mount on the first end 52 of the conditioning vessel 12. The connection member cap 66 preferably has a coupler 70 integrally formed thereon which is more preferably a Luer coupler. However, the Luer coupler 70 of the connection member cap 66 differs from the Luer couplers 26, 60 because the Luer coupler 70 does not function as a fluid port. The Luer coupler 70 is permanently closed at one end. The connection member cap 66 is mounted on the first end 52 of the conditioning vessel 12 by mating the Luer couplers 60 and 70 with one another. The mounted connection member cap 66 effectively stops up or blocks the Luer coupler 60, thereby substantially preventing fluid communication between the conditioning chamber 58 and the exterior of the conditioning chamber 58 via the Luer coupler 60.

Figure 7:
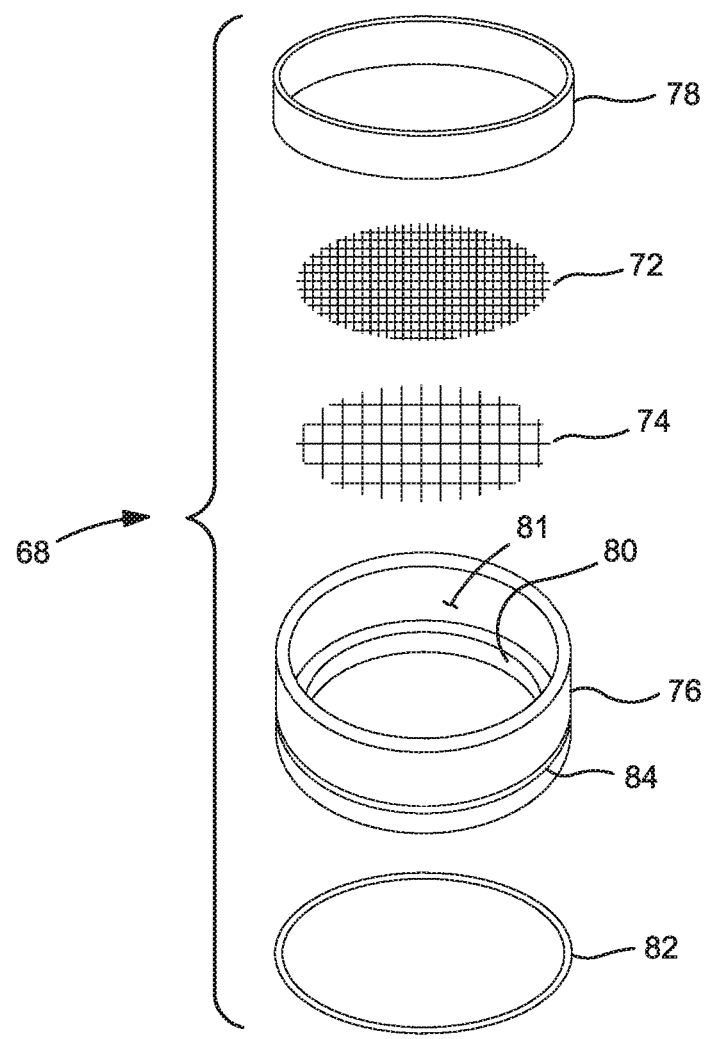
FIG. 7 is an exploded view of the filter cartridge shown in FIG. 6.

The filter cartridge 68 is sized and configured to continuously extend across essentially the entire circular cross-section of the conditioning chamber 58 and to be fixably snugly seated within the conditioning chamber 58 in abutment with the first end 52 of the conditioning vessel 12 and integral Luer coupler 60. In accordance with a preferred embodiment described with specific reference to FIG. 7, the filter cartridge 68 has a similar circular construction to the filter cartridge disclosed in U.S. patent application Ser. No. 15/154,885. The filter cartridge 68 comprises a filter element 72, an optional support element 74, a filter element mount 76 and a filter element retention member 78. The filter element mount 76 and filter element retention member 78 both have ring configurations and are both preferably formed from a disposable rigid or semi-rigid plastic. The outside diameters of the filter element 72, support element 74 and filter element retention member 78 are all preferably equal to one another and substantially equal to (i.e., identically equal to or at most only slightly less than) the inside diameter of the filter element mount 76 so that the filter element 72, support element 74 and filter element retention member 78 snugly nest within the filter element mount 76 when the filter cartridge 68 is assembled as described below. A circumferential ledge 80 is integrally formed with the inside edge of the filter element mount 76. The ledge 80 has a substantially smaller inside diameter than the outside diameters of the filter element 72, support element 74 and filter element retention member 78 so that the ledge 80 securely retains the filter element 72, support element 74 and filter element retention member 78 when they are nested in the filter element mount 76.

A preferred filter element 72 is a very thin, (i.e., having a very small thickness relative to the other components of the filter cartridge 68) disc-shaped structure. A preferred filter element 72 is more particularly a sieve or screen having a plurality of openings therethrough to define a porous open lattice or grid structure. The filter element 72 may be constructed from a mesh material having relatively larger pores such as a wire mesh or a fabric mesh or the like. Alternatively, a preferred filter element 72 is sheet of a continuous material having a plurality of openings in the form of relatively smaller pores or micro-pores therethrough. The alternate filter element 72 may be constructed from a sheet of a porous filtration medium, such as a porous sheet of cloth, fabric, polymer or other plastic or the like. In any case, the filter element 72 is preferably formed from a sterile, disposable, single-use material(s) that enables restricted fluid passage through it. In particular, the material of the filter element 72 is preferably selected to have filtration properties, e.g., mesh size or pore size, which permit most if not all of the undesirable non-fat liquids in the harvested fat to pass through the filter element 72 while preventing most if not all of relatively large solid or semi-solid particles in the harvested fat from passing through the filter element 72.

In some cases the material that is selected for fabrication of the filter element 72 may have structural characteristics that render the filter element 72 at least somewhat pliant and prone to deformation when a fluid force is applied to the filter element 72 without added support for it. In such cases the optional support element 74 is preferably provided having substantially the same shape and dimensions as the filter element 72. However, the support element 74 is preferably constructed from a rigid or semi-rigid material that is at least somewhat thicker and stronger than the material of the filter element 72, thereby providing the support element 74 with much greater strength and resistance to deformation when a fluid force is applied to it relative to the filter element 72. In sum, the support element 74 is preferably relatively substantially less pliant and correspondingly, relatively stiffer and rigid than the filter element 72.

A preferred construction of the support element 74 having the above-recited characteristics is a screen formed from a sterile, disposable, single-use material(s) such as a highly porous wire mesh that has a plurality of openings therethrough. The openings through the support element 74 are preferably substantially much larger than the corresponding openings through the filter element 72 so that the support element 74 is substantially less restrictive to fluid passage therethrough relative to the filter element 72. Thus, all of the undesirable materials in a harvested fat emulsion that pass through the filter element 72 also pass through the support element 74 when it is positioned downstream of the filter element 72 because of the substantially larger openings through the support element 74. Furthermore, it is self-evident that none of the desirable materials in a harvested fat emulsion that the filter element 72 blocks from passing through it ever reach the support element 74 when the support element 74 is positioned downstream of the filter element 72. As such, the primary, if not exclusive, function of the support element 74 is preferably to inhibit or prevent deformation of the filter element 72 under fluid pressure. Any filtration effect the support element 74 has, if at all, is preferably deminimis and secondary to its support function.

The filter cartridge 68 is preferably assembled by vertically stacking the filter element 72 and support element 74 one atop the other. The stacked filter element 72 and support element 74 are inserted into the interior of the filter element mount 76 until the support element 74 is firmly seated against the ledge 80 with the bottom of the filter element 72 resting atop the support element 74. The outer perimeters of the stacked filter element 72 and support element 74 are likewise seated against the interior circumferential walls of the filter element mount 76. Once the filter element 72 and support element 74 are in place within the filter element mount 76, the filter element retention member 78 is inserted into the interior of the filter element mount 76, stacked directly atop the filter element 72 and underlying support element 74 and attached to the filter element mount 76, preferably by substantially permanent attachment means such as light sensitive glue cured with UV light or the like. After assembly, a void space 81 remains in the filter cartridge 68 defined by the volume in the interior of the filter element mount 76 between the top surface of the filter element 72 and the top edge of the filter element mount 76.

The filter cartridge 68 also preferably includes a sealing element 82, such as an o-ring which is at least somewhat pliant and compressible. The sealing element 82 continuously encircles the outside face of the filter element mount 76 and deformably fits snugly against the inside face of the sidewall 56 of the conditioning vessel 12 to substantially prevent fluid leakage between the outside face of the filter element mount 76 and the inside face of the sidewall 56 when the filter cartridge 68 is seated in the conditioning chamber 58. A circumferential groove 84 is preferably formed in the outside face of the filter element mount 76 to retain a portion of the sealing element 82 therein.

In accordance with an alternate embodiment of a filter cartridge not shown, the optional support element 74 is omitted from the filter cartridge 68 and the remaining filter element 72 is self-supporting across its face within the filter cartridge 68. This alternate embodiment has particular utility in cases where the selected material of the filter element 72 has sufficient thickness and/or strength by itself without added support to resist substantial deformation when a fluid force is applied to it. All other components of the filter cartridge 68 apart from the support element 74 are present in this alternate embodiment of the filter cartridge. The alternate embodiment of the filter cartridge is assembled in substantially the same manner as described above with respect to the filter cartridge 68 except that the element support 74 is omitted and the filter element 72 alone is retained against the ledge 80 in the interior of the filter element mount 76 by means of the filter element retention member 78.

The plug 64 is configured to slidably displacably reside in the cylindrical conditioning vessel 12 in a manner described below. In accordance with a preferred embodiment described with reference to FIGS. 8-11, the plug 64 comprises a plug cap 86 and a plug body 88. The construction of the plug cap 86 preferably substantially resembles that of the plunger stopper 32 except that the plug cap 86 is configured for removably mounting on the plug body 88 rather than on the inner end 34 of the plunger 18. As such, the plug cap 86 is a unitary structure having a squat cylindrical shape and is preferably formed from an at least somewhat compressible, deformable elastic material such as rubber, synthetic rubber or other like elastomeric material, which is typically disposable.

With specific reference to FIGS. 8 and 9, the plug cap 86 has a first end 90, second end 92, an outer sidewall 94 extending perpendicularly between the first and second ends 90, 92 and a plurality of spaced-apart, compressible, deformable circumferential ribs 96 extending outwardly from the outer sidewall 94. The first end 90 of the plug cap 86 is open and has a retention lip 98 extending around its circumferential edge in the manner of the open end 38 of the plunger stopper 32. However, unlike the closed end 40 of the plunger stopper 32, the second end 92 of the plug cap 86 is not entirely closed. Instead the second end 92 has an aperture 100 extending therethrough which is narrower than the open first end 90 and renders the second end 92 only partially closed. The second end 92, outer sidewall 94 and retention lip 98 in combination define an interior cavity of the plug cap 86, termed a body retention chamber 102, which is sized and configured in correspondence with the peripheral shape of the plug body 88. The inside diameter of the retention lip 98 is preferably substantially less than the diameter of the inner sidewall of the body retention chamber 102.

The plug cap 86 is removably mounted on the plug body 88 by positioning the first end 90 of the plug cap 86 above the plug body 88. The plug cap 86 is press fitted down onto the plug body 88 causing the retention lip 98 to deform around the plug body 88, thereby enabling the plug body 88 to slip past the retention lip 98 into the body retention chamber 102. The retention lip 98 retains the plug body 88 in the body retention chamber 102 so that the plug cap 86 substantially encloses the plug body 88.

The diameter of the outer sidewall 94 of the plug cap 86 is preferably about equal to the diameter of the conditioning vessel 12. In the present case "about equal to" means that the diameter of the outer sidewall 94 of the plug cap 86 is preferably only very slightly smaller than the diameter of the conditioning vessel 12. In contrast, the outside diameters of the compressible ribs 96 of the plug cap 86 are preferably slightly greater than the diameter of the conditioning vessel 12 when the ribs 96 are uncompressed. The slightly oversize fit of the ribs 96 relative to the diameter of the conditioning vessel 12 deforms and compresses the ribs 96 against the sidewall 56 of the conditioning vessel 12. Nevertheless, the material of the plug cap 86 exhibits sufficient structural integrity that the ribs 96 provide a reliably secure fluid tight seal between the outside edge of the plug cap 86 and the sidewall 56 of the conditioning vessel 12. Accordingly, the plug cap 86 nests snugly within the interior of the conditioning vessel 12 without fluid leakage past the plug cap 86, but is still slidably displacable therein relative to the conditioning vessel 12 when a sufficient force is applied to the plug 64.

With specific reference to FIGS. 10 and 11, the plug body 88 is a unitary structure preferably formed in its entirety from one or more materials, such as metal or plastic, which are generally characterized as durable, strong, rigid, wear-resistant, non-corrosive, smooth, non-porous, substantially inert and having a surface which does not readily retain contaminants. The material(s) of the plug body 88 having the above-recited characteristics may either be a sterile, disposable, single-use material(s) similar to the plastic of the filter element mount 76 and filter element retention member 78 or may be a heat-resistant reusable material(s) which is suitable for autoclaving. A preferred material of the plug body 88 is a reusable stainless steel.

The plug body 88 preferably has a unitary construction which includes a plug retention cap 104, a connector segment 106, a coupler interface 108 and a connection member 110, all integrally formed with one another in series. The connector segment 106 and coupler interface 108 extend between the plug retention cap 104 on one side of the plug body 88. The connection member 110 is on the other side of the plug body 88. The plug retention cap 104 is sized and conically configured to be received and releasably retained in the body retention chamber 102 of the plug cap 86. As such, the outer peripheral shape of the plug retention cap 104 substantially conforms to the inside shape of the body retention chamber 102. Placement and releasable retention of the plug retention cap 104 in the body retention chamber 102 is effected in the manner described above.

The coupler interface 108 is preferably configured as a planar disk or circular plate. The connector segment 106 is preferably configured as a cylinder with a first end and a second end opposite the first end. The longitudinal axis of the plug body 88 coincides with central cylindrical axes of the plug retention cap 104, connector segment 106, coupler interface 108 and connection member 110 and is substantially perpendicular to the plane of the coupler interface 108. The connection member 110 is preferably a Luer coupler which is part of an internal cylindrical fluid passageway 112 continuously extending through the entire length of the plug body 88 along its longitudinal axis. The fluid passageway 112 serially aligns with the aperture 100 of the plug cap 86 when the plug body 88 is fitted therein to function as a second port for fluid or other materials to enter or exit the conditioning chamber 58. Accordingly, the fluid passageway 112 provides fluid communication between the conditioning chamber 58 and the exterior of the conditioning chamber 58.

The plug 64 acts in the manner of a piston slidably displacable within the conditioning vessel 12. The plug 64 is displacable in the outward expansion direction away from the first end 52 of the conditioning vessel 12 by applying a fluid force to the plug 64 in the same outward expansion direction. Conversely, the plug 64 is displacable in an opposite inward contraction direction toward the first end 52 of the conditioning vessel 12 by applying a manual force to the plug 64 in this same inward contraction direction. It is apparent that as the plug 64 is displaced, the variable position of the plug 64 relative to the fixed conditioning vessel 12 including its sidewall 56 and first end 52 with integrally formed Luer coupler 60, defines the variable-volume of the conditioning chamber 58. The volume of the conditioning chamber 58 increases as the degree of displacement of the plug 64 in the outward expansion direction increases and the volume of the conditioning chamber 58 decreases as the degree of displacement of the plug 64 in the inward contraction direction increases.

It is noted that the Luer couplers 26, 60, 110 and fluid passageway 112 of the plug body 88 described above are relatively wide, having substantially greater diameters and corresponding cross-sectional areas than conventional syringe cannulas.

As such, the Luer couplers 26, 60, 110 and fluid passageway 112 preferably do not act as flow restricters when materials such as a harvested fat emulsion are conveyed through them in accordance with the method described below. The Luer couplers 26, 60, 110 and fluid passageway 112 are sufficiently wide that they are not easily clogged or otherwise prone to a flow impeding build-up of a harvested fat emulsion when it flows through them. Furthermore, the Luer couplers 26, 60, 110 and fluid passageway 112 are sufficiently wide that passing a harvested fat emulsion through them preferably does not substantially alter the physical properties of the harvested fat emulsion by boundary effects or other mechanisms.

FIGS. 12 and 13 show an alternate embodiment of a plug which is designated 164. The plug 164 has a plug body 188 with a similar construction to the embodiment of the plug body 88 shown in FIGS. 8-11. In particular, the plug body 188 preferably has a unitary construction which includes a plug retention cap 204, a connector segment 206, a coupler interface 208 and a connection member 210, all integrally formed with one another in series. The plug body 188 is preferably constructed from one or more materials having the same characteristics as the plug body 188. A preferred material(s) of the plug body 188 is a sterile, disposable, single-use material similar to the plastic of the filter element mount 76 and filter element retention member 78. The plug retention cap 204, connector segment 206, connection member 210 and fluid passageway 212 are all substantially identical to the corresponding components of the plug body 88. The coupler interface 208 is preferably configured as a planar disk or circular plate in the same manner as the coupler interface 108, but has a diameter substantially equal to the diameter of the plug retention cap 204. The plug 164 differs from the plug 64 because the plug 164 substitutes a sealing element 186 for the plug cap 186 of plug 64. The sealing element 186 is an o-ring mounted around the periphery of the plug body 188, encircling the connector segment 206 between the retention cap 204 and coupler interface 208.

The sealing element 186 is preferably formed from the same disposable material as the plug cap 86. The outside diameter of the sealing element 186 is preferably slightly greater than the diameter of the conditioning vessel 12 when the sealing element 186 is uncompressed and the slightly oversize fit of the sealing element 186 relative to the diameter of the conditioning vessel 12 deforms and compresses the sealing element 186 against the sidewall 56 of the conditioning vessel 12 in essentially the same manner as the ribs 96 of the plug cap 86 to provide a reliably secure fluid tight seal between the sealing element 186 and the sidewall 56 of the conditioning vessel 12. Accordingly, the sealing element 186 nests snugly within the interior of the conditioning vessel 12 without fluid leakage past the sealing element 186, but is still slidably displacable therein relative to the conditioning vessel 12 when a sufficient force is applied to the plug 164. It is apparent from the above description that the plug 164 is configured to function in substantially the same manner as the plug 64. As such, the functional description of the plug 64 recited herein applies equally to the plug 164 which may be utilized in the conditioning vessel 12 as an alternative to the plug 64.

METHOD OF USE

An embodiment of a fat conditioning method is described hereafter with reference to FIGS. 1 and 14-20. The instant embodiment of the fat conditioning method is more particularly characterized as a fat washing method. Although the instant embodiment of the present fat washing method utilizes the above-described fat conditioning apparatus 10 including the conditioning vessel 12 and transfer syringes 14a, 14b for purposes of illustration, it is understood that the present method is not limited to the use of any one specific apparatus or system of apparatuses. With initial reference to FIG. 1, the variable-volume conditioning chamber 58 of the conditioning vessel 12 preferably has a maximum volumetric capacity substantially greater than the maximum volumetric capacity of each variable-volume transfer syringe 14a, 14b individually. Stated alternatively, the conditioning chamber 58 of the conditioning vessel 12 preferably has a maximum volumetric capacity at least equal to, and more preferably substantially greater than, the maximum total volumetric capacity of both transfer syringes 14a, 14b combined. For example, the conditioning chamber 58 of the conditioning vessel 12 shown in FIG. 1 has a maximum volumetric capacity that is 3 times greater than the maximum volumetric capacity of each transfer syringe 14a, 14b individually and 1.5 times greater than the maximum total volumetric capacity of both transfer syringes 14a, 14b combined. As such, the conditioning chamber 58 of the conditioning vessel 12 shown in FIG. 1 has a maximum volumetric capacity of about 60 cc and each transfer syringe 14a, 14b has a maximum individual volumetric capacity of about 20 cc for a maximum combined total volumetric capacity of about 40 cc.

At the inception of the present method, the transfer syringe 14a contains 20 cc, i.e., its maximum individual volumetric capacity, of a harvested fat emulsion. An emulsion by definition is a mixture of two or more liquids that are dispersed with one another although they are not normally miscible or soluble with one another. As such, the instant harvested fat emulsion includes fat in a liquid state dispersed within one or more non-fat hydrophilic (i.e., oleophobic) and/or hydrophobic (i.e., oleophilic) liquids. The fat contained within the harvested fat emulsion may include the full spectrum of fat particle sizes, wherein the fat particles are generally in the form of liquid globules. In addition to being a mixture of liquids, the instant harvested fat emulsion may also include relatively large non-fat solid and semi-solid particles. In any case, the resulting harvested fat emulsion is typically cloudy in appearance.

The harvested fat emulsion is preferably freshly harvested from a patient and in many cases may still be in its raw state after removal from the patient. By raw state, it is meant that the harvested fat emulsion in essentially the same condition as when it was removed from a patient during the fat harvesting procedure and has not yet been subjected to any fat conditioning procedures. Nevertheless, it is further within the scope of the present method that the harvested fat emulsion in the transfer syringe 14a is not in its raw state, but has undergone some sort of alternate conditioning procedure prior to practice of the present fat conditioning method. In any case, it is understood that the present method is intended to render the harvested fat emulsion that is the subject of the present method more desirable for re-injection into a patient.

It is further noted that the transfer syringe 14b contains 20 cc, i.e., its maximum individual volumetric capacity, of a washing liquid at the inception of the present method. The washing liquid is preferably a clear aqueous liquid such as water, distilled water or a saline solution substantially free from particulates. In contrast to the transfer syringes 14a, 14b, the conditioning chamber 58 of the conditioning vessel 12 is initially empty with its variable volume at a value of about 0 cc. As such, the plug 64 is in a fully depressed position abutting the filter cartridge 68 adjacent to the first end 52 of the conditioning vessel 12. The filter cartridge 68 is oriented within the conditioning vessel 12 such that the filter element 72 and support element 74 are stacked with one another and the filter element 72 and void space 81 are nearer the second end 54 while the support element 74 is nearer the first end 52 of the conditioning vessel 12.

Figure 14:
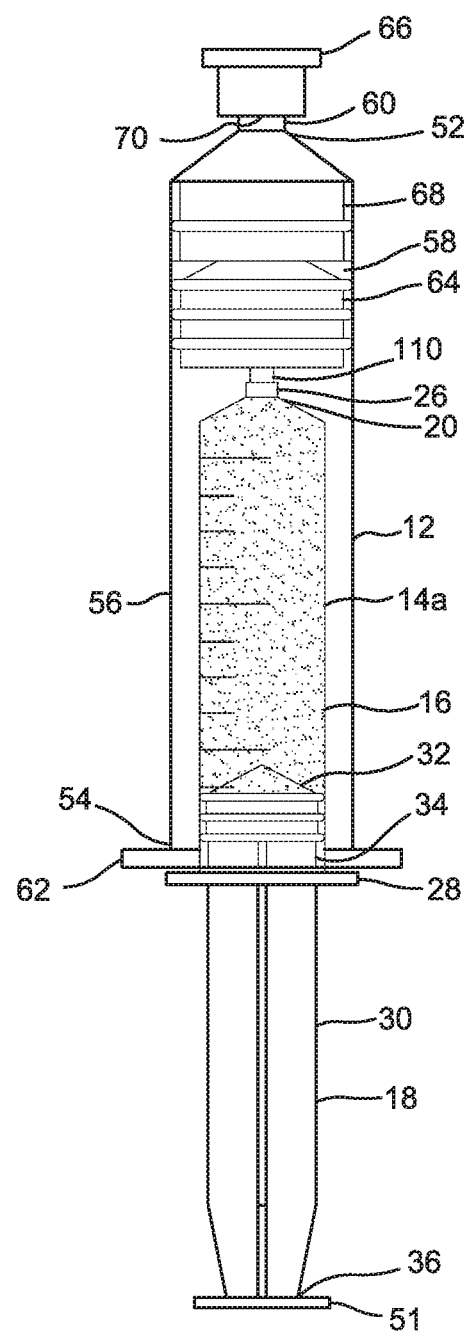
FIGS. 14-20 show the sequential steps in a method of use for the fat conditioning apparatus of FIG. 1.

With reference to FIG. 14, the method is initiated by coupling the female Luer coupler 60 on the first end 52 of the conditioning vessel 12 with the male Luer coupler 70 of the connection member cap 66 by screwing the external threads of the Luer coupler 70 into the internal threads of the Luer coupler 60 to cover or cap the Luer coupler 60 and effectively block fluid flow between the conditioning chamber 58 and its exterior via the first end 52 of the conditioning vessel 12. The practitioner then inserts the first end 20 of the barrel 16 of the transfer syringe 14a into the interior of the conditioning vessel 12 and couples the female Luer coupler 26 of the transfer syringe 14a with the male Luer coupler 110 of the plug body 88 by screwing the external threads of the Luer coupler 110 into the internal threads of the Luer coupler 26 so that the interior of the barrel 16 of the transfer syringe 14a and the conditioning chamber 58 of the conditioning vessel 12 are in fluid communication with one another.

Figure 15:
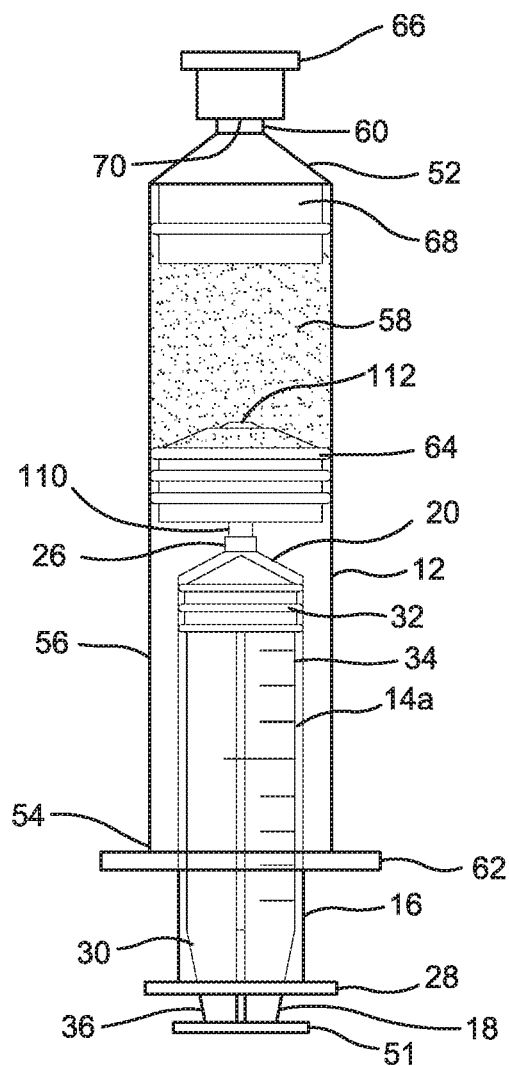

The practitioner applies a manual pushing force on the plunger 18, more particularly on the second end 36 of the plunger 18, and more particularly still on the plunger finger hold 51 of the transfer syringe 14a while maintaining the connection member cap 66 in place on the Luer coupler 60. The pushing force displaces the plunger 18 in the inward contraction direction toward the first end 20 of the barrel 16 of the transfer syringe 14a and continues until the plunger stopper 32 abuts the first end 20 of the barrel 16. The plunger 18 acts as a piston to displace the entire contents of the barrel 16 in the same inward contraction direction, thereby substantially emptying the entire volume of the harvested fat emulsion in the barrel 16 into the conditioning chamber 58 via the Luer couplers 26, 110 and the fluid passageway 112, i.e., 20 cc of the harvested fat emulsion. The fluid pressure of the harvested fat emulsion that is displaced into the conditioning chamber 58 exerts a fluid force on the face of the plug 64 nearest the first end 52 of the conditioning vessel 12 in the outward expansion direction that is opposite the inward contraction direction of the pushing force and causes the harvested fat emulsion to displace the plug 64 in the conditioning vessel 12 in this outward expansion direction. As a result, the variable volume of the conditioning chamber 58 expands as shown in FIG. 15 to a volume about equal to the volume of harvested fat emulsion injected into the conditioning chamber 58 from the transfer syringe 14a.

It is noted that throughout the duration of the present method, the filter cartridge 68 is snugly maintained within the conditioning vessel 12 in a static stationary position relative to the conditioning vessel 12. This static position of the filter cartridge 68 is within the conditioning chamber 58 in abutment with the first end 52 of the conditioning vessel 12. The filter element 72 in the filter cartridge 68 is correspondingly within the conditioning chamber 58 and forms an interface between the conditioning chamber 58 and the Luer coupler 60. Thus, the filter element 72 in cooperation with the Luer coupler 60, forms a fluid outlet from the conditioning chamber 58, and correspondingly from the conditioning vessel 12, when the Luer coupler 60 is uncovered or uncapped as described below.

Figure 16:
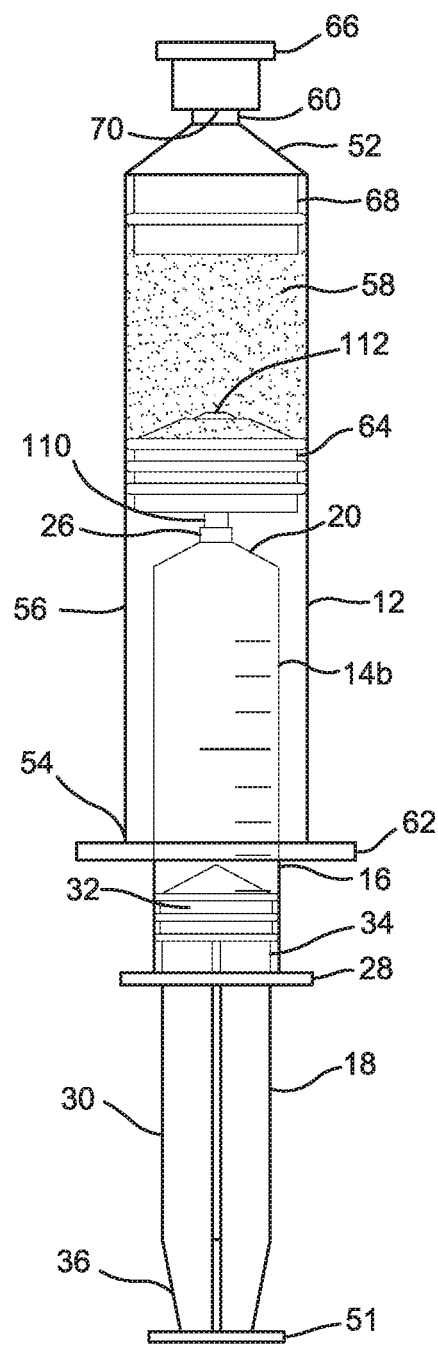

After emptying the transfer syringe 14a, the practitioner uncouples the Luer coupler 26 of the transfer syringe 14a from the Luer coupler 110 of the conditioning vessel 12, withdraws the empty transfer syringe 14a from the interior of the conditioning vessel 12 while maintaining the connection member cap 66 in place on the Luer coupler 60 and sets the empty transfer syringe 14a aside for proper disposal. The practitioner inserts the first end 20 of the barrel 16 of the transfer syringe 14b into the interior of the conditioning vessel 12 and couples the Luer coupler 26 of the transfer syringe 14b with the Luer coupler 110 of the plug body 88 in substantially the same manner as described above with respect to the transfer syringe 14a so that the interior of the barrel 16 of the transfer syringe 14b and the conditioning chamber 58 of the conditioning vessel 12 are in fluid communication with one another as shown in FIG. 16.

The practitioner applies a manual pushing force in the inward contraction direction on the plunger 18, more particularly on the second end 36 of the plunger 18, and more particularly still on the plunger finger hold 51 of the transfer syringe 14b in substantially the same manner as described above with respect to the transfer syringe 14a. The plunger 18 displaces the entire contents of the barrel 16 in the inward contraction direction, thereby substantially emptying the entire volume of the washing liquid in the barrel 16 of the transfer syringe 14b into the conditioning chamber 58 of the conditioning vessel 12, i.e., 20 cc of the washing liquid. Displacement of the washing liquid into the conditioning chamber 58 from the barrel 16 of the transfer syringe 14b via the Luer couplers 26, 110 and the fluid passageway 112 of the plug body 88 causes the washing liquid to mix with the harvested fat emulsion already residing therein.

Figure 17:
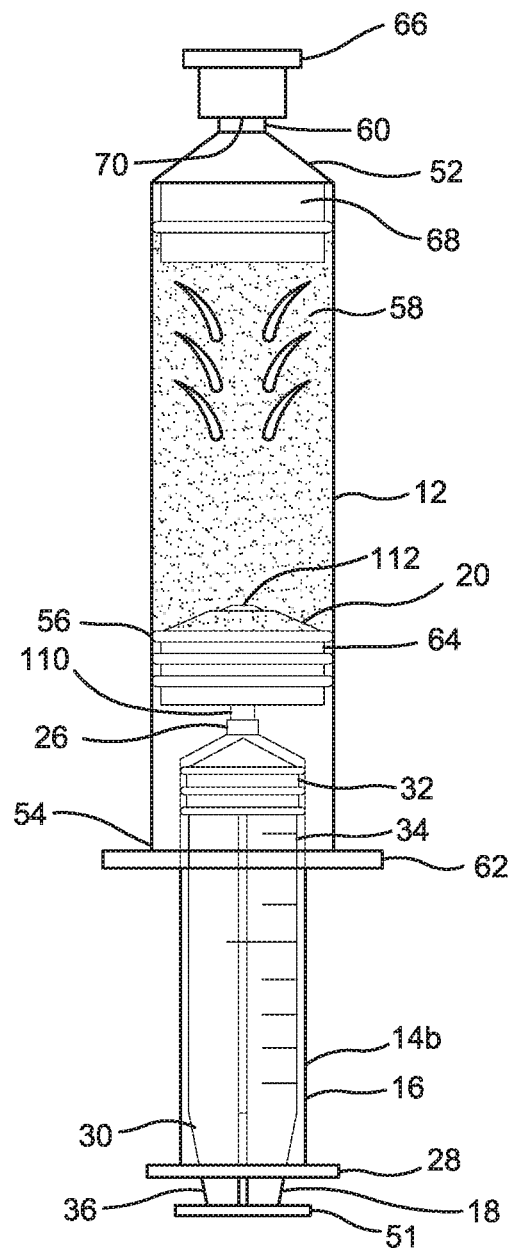

The fluid pressure of the washing liquid that is newly-displaced into the conditioning chamber 58 exerts a fluid force on the face of the plug 64 in the outward expansion direction similar to that exerted by the harvested fat emulsion that causes the washing liquid to displace the plug 64 still further in the outward expansion direction. As a result, the variable volume of the conditioning chamber 58 further expands as shown in FIG. 17 to a volume about equal to the total volume of the harvested fat emulsion and washing liquid injected into the conditioning chamber 58 from both of the transfer syringes 14a, 14b, respectively, i.e., 40 cc. Thus, the final expanded volume of the conditioning chamber 58 is 2 times that of the maximum volumetric capacity of the transfer syringes 14a, 14b individually and substantially equal to that of the maximum volumetric capacity of both transfer syringes 14a, 14b in combination.

Figure 18:
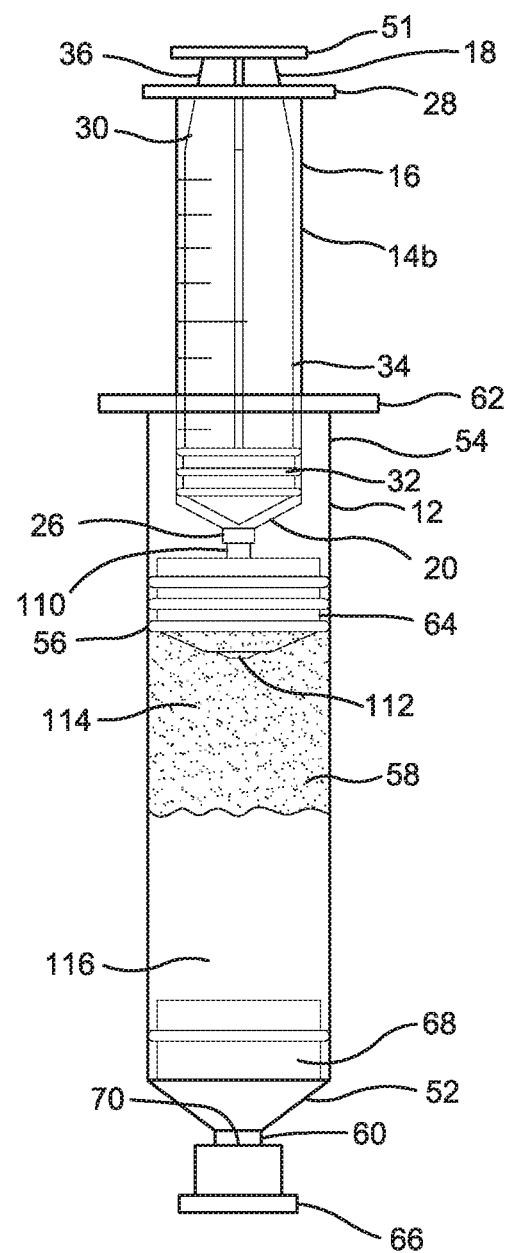

To facilitate, i.e., expedite and/or enhance, complete mixing and contacting of the harvested fat emulsion and the washing liquid, the practitioner may briefly agitate the contents of the conditioning chamber 58, e.g., by shaking and/or oscillating the conditioning vessel 12 for a few seconds, while maintaining the connection member cap 66 in place on the Luer coupler 60 of the conditioning vessel 12 and the transfer syringe 14b in place on the Luer coupler 110 of the plug body 88. The resulting mixture of harvested fat emulsion and washing liquid residing in the expanded conditioning chamber 58 promptly stratifies into two distinct and discrete fractions 114, 116 as shown in FIG. 18 while the conditioning vessel 12 is preferably vertically oriented with the first end 52 positioned below the second end 54 of the conditioning vessel 12. The filter cartridge 68 is correspondingly vertically oriented within the conditioning vessel 12 so that the filter element 72 is stacked above the support element 74 nearer the top second end 54 and the support element 74 is stacked beneath the filter element 72 nearer the bottom first end 52 of the conditioning vessel 12. Stratification typically occurs essentially instantaneously, i.e., either immediately or within a few seconds after mixing, after which time the practitioner is free to continue with the next step of the present method. Although not generally necessary, the practitioner may optionally perform another step in addition to or in place of the essentially instantaneous stratification step described above, wherein the mixture of harvested fat emulsion and washing liquid is allowed to rest undisturbed within the conditioning chamber 58 in the above-described vertical orientation for a desired rest period typically on the order of half a minute or so before continuing with the next step.

In any case, the first fraction 114 resulting from stratification of the mixture of harvested fat emulsion and washing liquid is termed the fat fraction and the second fraction 116 is termed the remainder fraction. The fat fraction 114 resides in the top of the conditioning chamber 58 and the remainder fraction 116 resides in the bottom of the conditioning chamber 58 when it is vertically oriented as described above. The fat fraction 114 is relatively cloudy in appearance due inter alia to the presence of most, if not all, fat particles in the harvested fat emulsion. As such, the fat fraction 114 preferably contains the majority, and more preferably the bulk, if not essentially all, of the materials in the harvested fat emulsion, that are more desirable for re-injection. More particularly, the fat fraction 114 preferably contains the majority, and more preferably the bulk, if not essentially all, of the fat from the harvested fat emulsion. The fat fraction 114 also preferably contains very little, if any, of the contaminants from the harvested fat emulsion and the washing liquid, thereby characterizing the fat fraction 114 as fat-rich and further characterizing it as both contaminant-lean and wash liquid-lean.

The remainder fraction 116 is an infranatant fluid that is relatively clear in appearance due inter alia to the absence of most if not all fat particles from the harvested fat emulsion. As such, the remainder fluid 116 preferably contains the majority, and more preferably the bulk, if not essentially all, of the materials in the harvested fat emulsion that are less desirable for re-injection. More particularly, the remainder fraction 116 preferably contains the majority, and more preferably the bulk, if not essentially all, of the washing liquid and the contaminants from the harvested fat emulsion, such as tumescent fluid and blood that associate with the washing liquid, and contains very little, if any, of the fat from the harvested fat emulsion, thereby characterizing the remainder fraction 116 as fat-lean and further characterizing it as both contaminant-rich and wash liquid-rich.

Performance of the stratification step in the present method is not limited to any particular mechanism. Nevertheless, the density and polarity of the materials making up the mixture of harvested fat emulsion and washing liquid in the conditioning chamber 58 are among the factors that are believed to effect stratification of the mixture into the fat fraction 114 and the remainder fraction 116. With respect to density, many of the materials in the mixture that are less dense, e.g., fat, are more desirable for re-injection and tend to rise to the top of the mixture and partition into the fat fraction 114. In contrast, many of the materials in the mixture that are more dense, e.g., the washing liquid, tumescent fluid and blood, are less desirable for re-injection and tend to settle to the bottom of the mixture and partition into the remainder fraction 116 under the force of gravity. With respect to polarity, the materials in the mixture that are more hydrophobic or oleophilic, e.g., nanofat, are likewise more desirable for re-injection and are drawn by materials of like polarity to the fat fraction 114. In contrast, the materials in the mixture that are more hydrophilic, e.g., the washing liquid, tumescent fluid and blood, are likewise less desirable for re-injection and are drawn by materials of like polarity to the remainder fraction 116.

Figure 19:
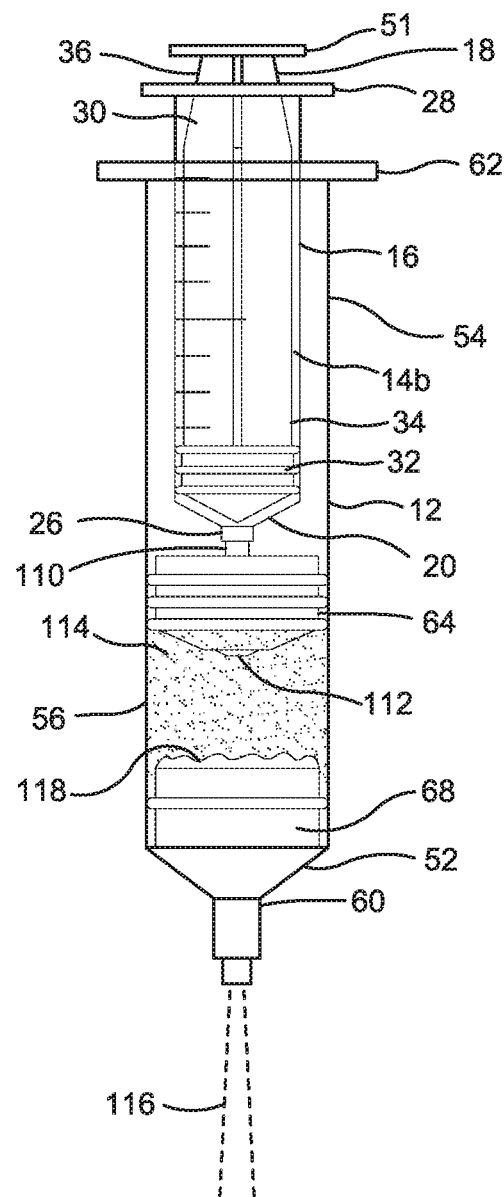

With reference to FIG. 19, the practitioner uncouples the Luer coupler 70 of the connection member cap 66 from the Luer coupler 60 on the first end 52 of the conditioning vessel 12 after stratification, thereby providing fluid communication between the conditioning chamber 58 and the external environment and enabling fluid flow from the conditioning chamber 58 to its exterior via the filter cartridge 68 and the first end 52 of the conditioning vessel 12. With the Luer coupler 60 uncapped and the conditioning vessel 12 preferably in the same vertical orientation as FIG. 18, the practitioner applies a steady, even and continuous manual pushing force on the plunger 18, more particularly on the second end 36 of the plunger 18, and more particularly still on the plunger finger hold 51. The pushing force does not move the plunger 18 relative to barrel 16 of the transfer syringe 14b because the plunger 18 is already fully depressed into the empty barrel 16 with the plunger stopper 32 abutting the first end 20 of the barrel 16. However, the pushing force moves the entire transfer syringe 14b relative to the conditioning vessel 12 in a manner described below. It is further noted that maintaining the plunger stopper 32 in abutment with the first end 20 of the barrel 16 prevents backflow from the conditioning chamber 58 into the transfer syringe 14b.

Each increment of time that the pushing force is applied on the plunger 18 results in displacement of the transfer syringe 14b and correspondingly the plug 64, which is connected thereto, an incremental distance in the inward contraction direction into the conditioning vessel 12 toward its first end 52. This causes an incremental contraction of the variable volume of the conditioning chamber 58. Prior to contraction of the conditioning chamber 58, the entirety of the remainder fraction 116 resides in the conditioning chamber 58 between the fat fraction 114 and the uncapped Luer coupler 60. As such, the remainder fraction 116 is more proximal to the Luer coupler 60 than is the fat fraction 114. Therefore, incremental contraction of the conditioning chamber 58 correspondingly causes displacement of an incremental portion of the remainder fraction 116 across the upstream filter element 72 in the filter cartridge 68 and discharge of the incremental portion of the remainder fraction 116 from the conditioning chamber 58 through the uncapped downstream Luer coupler 60 into the external environment.

The sum of these incremental contractions, which are performed in a continuum without interruption, results in the plug 64 traveling a sufficient displacement distance into the conditioning vessel 12 to discharge substantially all of the remainder fraction 116 in the conditioning chamber 58 across the upstream filter element 72 and out of the conditioning chamber 58 via the uncapped downstream Luer coupler 60 as a conditioning chamber effluent. It is noted that the practitioner desirably takes care to apply the manual pushing force on the plunger 18 in a manner that smoothly and continuously displaces the transfer syringe 14b and plug 64 so that the conditioning chamber contents are minimally agitated, thereby maintaining stratification of the re-injection and remainder fractions 114, 116 and minimizing or eliminating cross-contamination between the two fractions 114, 116 throughout discharge of the remainder fraction 116 from the conditioning chamber 58.

The determination of when to withdraw the pushing force on the plunger 18 and terminate discharge of the conditioning chamber effluent from the conditioning chamber 58 relies on the practitioner's visual monitoring of the appearance of the conditioning chamber effluent exiting the Luer coupler 60 and simultaneously monitoring of the appearance of the material remaining in the conditioning chamber 58. The practitioner promptly withdraws the pushing force on the plunger 18 and terminates corresponding displacement of the transfer syringe 14b and plug 64 when the appearance of the conditioning chamber effluent transitions from substantially clear to substantially cloudy and/or relatively very little or no clear liquid remains visible in the conditioning chamber 58.

The practitioner may properly dispose of the remainder fraction 116 as a waste or save it for use in some other application. In any case, the fat fraction 114 is retained in the conditioning chamber 58 as a fat-containing emulsion for subsequent recovery and use as a desirable re-injection material in a manner described below. As described above, the remainder fraction 116 passes across the filter element 72 during discharge of the remainder fraction 116 from the conditioning chamber 58. The filter element 72 removes particles suspended in the remainder fraction 116 that are too large to pass through the openings in the filter element 72 and are a by-product of the present method. These particles are typically relatively dense, opaque or translucent solids or semi-solids and are retained in the conditioning chamber 58 as a filter cake 118 on the face of filter element 72 most proximal to the second end 54 of the conditioning vessel 12. The filter cake 118 typically fills only a very small portion of the void space 81 in the filter cartridge 68. However, its size is somewhat exaggerated in FIGS. 19 and 20 for purposes of illustration. The filter element 72 may also impede any desirable particles suitable for re-injection that belong in the fat fraction 114 and/or that stray into the remainder fraction 116 and/or that reside at the interface between the fat fraction 114 and remainder fraction 116 from being inadvertently discharged from the conditioning chamber 58 with the remainder fraction 116.

Figure 20:
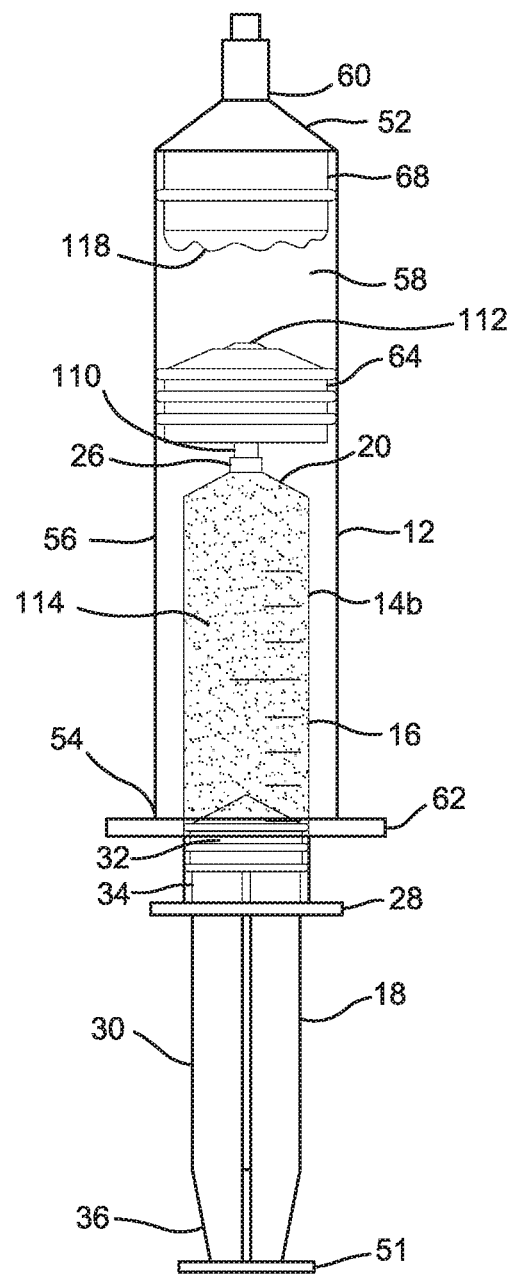

With reference to FIG. 20, the practitioner initiates recovery of the fat fraction 114 from the conditioning chamber 58 once the remainder fraction 116 is expelled from the conditioning chamber 58. Before recovering the fat fraction 114 from the conditioning chamber 58, however, it may in some cases be desirable to reverse the vertical orientation of the conditioning vessel 12 from that shown in FIG. 19 to that shown in FIG. 20, wherein the first end 52 of the conditioning vessel 12 is below the second end 54. Reversal of the vertical orientation of the conditioning vessel 12 is effected by gently rotating the conditioning vessel 12 180° with the transfer syringe 14b still in place on the Luer coupler 110 of the plug body 88. Care is taken not to disturb the filter cake 118 and cause it to mix with the fat fraction 114 during rotation of the conditioning vessel 12.

Recovery of the fat fraction 114 substantially free of the remainder fraction 116 from the conditioning chamber 58 is effected by applying a manual pulling force to the plunger 18, more particularly to the second end 36 of the plunger 18, and more particularly still to the plunger finger hold 51 of the transfer syringe 14b, thereby displacing the plunger 18 relative to the barrel 16 of the transfer syringe 14b in the outward expansion direction away from the first end 20 of the barrel 16. It is noted that displacing the plunger 18 relative to the barrel 16 in the outward expansion direction typically does not cause displacement of the plug 64 within the conditioning vessel 12 nor does it correspondingly cause a change in the volume of the conditioning chamber 58 which may remain constant throughout recovery of the fat fraction 114.

Displacement of the plunger 18 relative to the barrel 16 in the outward expansion direction increases the volume of the fluid retention chamber in the interior of the barrel 16 of the transfer syringe 14b, thereby drawing the fat fraction 114 residing in the conditioning chamber 58 therefrom into the fluid retention chamber of the barrel 16 via the Luer couplers 26, 110 and the fluid passageway 112 of the plug body 88. The practitioner continues applying the pulling force to the plunger 18, thereby continuing displacement of the plunger 18 in the outward expansion direction until substantially all of the fat fraction 114 is withdrawn from the conditioning chamber 58 while the filter cake 118 remains caked against the face of the filter element 72 in the conditioning chamber 58. The practitioner desirably takes care to apply the manual pulling force to the plunger 18 in a manner that is smooth and continuous so that the conditioning chamber contents are minimally agitated, thereby maintaining separation of the fat fraction 114 from the filter cake 118 and minimizing or eliminating cross-contamination between the fat fraction 114 throughout recovery of the fat fraction 114 from the conditioning chamber 58.

The volume of the recovered fat fraction 114 in the transfer syringe 14b is generally less than the volume of harvested fat emulsion injected into the conditioning chamber 58 from the transfer syringe 14a because the volume of the harvested fat emulsion associated with the washing liquid in the remainder fraction 116 and the volume of the filter cake 118 are subtracted from the initially injected volume of the harvested fat emulsion to arrive at the volume of the fat fraction 114 recovered in the transfer syringe 14b from the conditioning chamber 58.

Upon recovering substantially all of the fat fraction 114 from the conditioning chamber 58 and placing the recovered fat fraction 114 in the transfer syringe 14b, the practitioner uncouples the Luer coupler 26 of the transfer syringe 14b from the Luer coupler 110 of the conditioning vessel 12 and withdraws the transfer syringe 14b from the conditioning vessel 12. The Luer coupler 26 of the transfer syringe 14b may then be fitted with a suitable sterile cannula (not shown) enabling the transfer syringe 14b and the fat fraction 114 contained therein to be utilized in a fat re-injection procedure on a patient. If the fat fraction 114 is re-injected into the same patient as the harvested fat emulsion has been harvested from, the fat re-injection procedure is autologous.

The filter cake 118 retained in the conditioning chamber 58 may be properly disposed as a waste or saved for some other application outside the scope of the present method. It is apparent that the above-described fat conditioning method is preferably and advantageously a closed and anaerobic procedure.

In an alternate embodiment of the present fat washing method, the order in which the mixture of harvested fat emulsion and washing liquid are injected into the conditioning chamber 58 is reversed. Thus, the washing liquid is injected into the conditioning chamber 58 first followed by injection of the harvested fat emulsion into the conditioning chamber 58. In substantially all other respects, this alternate fat conditioning method is essentially the same as the above-described fat conditioning method.

In another alternate embodiment of the present fat washing method, a single transfer syringe 14 is employed to inject the harvested fat emulsion and washing liquid into the conditioning chamber 58 and to recover the fat fraction 114 from the conditioning chamber 58. After the transfer syringe 14 is emptied by injecting the harvested fat emulsion into the conditioning chamber 58, the same transfer syringe 14 is recharged with the washing liquid, which is then injected into the conditioning chamber 58. Thereafter, instant embodiment is essentially the same as the above-described embodiment of the fat washing method. It is also understood that the injection order of the instant embodiment can be reversed so that the washing liquid is injected into the conditioning chamber 58 first followed by injection of the harvested fat emulsion into the conditioning chamber 58.

An alternate fat conditioning method is described hereafter that is more particularly characterized as a fat sizing method. The instant fat sizing method utilizes the above-described fat conditioning apparatus 10 including the conditioning vessel 12 and transfer syringes 14a, 14b. The fat sizing method may be performed in serial combination with other fat conditioning procedures. For example, the harvested fat emulsion can be washed as described above before performing the instant sizing method on the fat fraction resulting from the fat washing method.

The initial steps of the fat sizing method are essentially the same as those described above with respect to the fat washing method shown in FIGS. 14 and 15 except that the transfer syringe 14a may be filled with any number of alternate fat-containing emulsions. For example, the transfer syringe 14a may contain a harvested fat emulsion or a fat fraction resulting from washing a harvested fat emulsion. In any case, once the contents of the transfer syringe 14a are transferred into the conditioning chamber 58 as shown in FIG. 15, the instant fat sizing method omits the steps of the fat washing method shown in FIGS. 16-18. In particular, the Luer coupler 26 of the empty transfer syringe 14a is maintained coupled to the Luer coupler 110 of the plug body 88 with the plunger 18 fully depressed into the empty barrel 16 of the transfer syringe 14a and the plunger stopper 32 abutting the first end 20 of the barrel 16. Thereafter, the practitioner uncouples the Luer coupler 70 of the connection member cap 66 from the Luer coupler 60 on the first end 52 of the conditioning vessel 12 and couples the Luer coupler 26 of the transfer syringe 14b, which is likewise empty with its plunger 18 fully depressed, to the Luer coupler 60 on the first end 52 of the conditioning vessel 12.

Fat sizing is effected by applying a manual pulling force to the plunger 18 of the transfer syringe 14b, more particularly to the second end 36 of the plunger 18, and more particularly still to the plunger finger hold 51 of the transfer syringe 14b, thereby displacing the plunger 18 relative to the barrel 16 of the transfer syringe 14b in the outward expansion direction away from the first end 20 of the barrel 16. Displacement of the plunger 18 relative to the barrel 16 in the outward expansion direction increases the volume of the fluid retention chamber in the interior of the barrel 16 of the transfer syringe 14b, thereby drawing the harvested fat emulsion residing in the conditioning chamber 58 across the upstream filter element 72 in the filter cartridge 68. The filter element 72 is preferably selected in accordance with the teaching of our co-pending U.S. patent application Ser. No. 15/154,885 to increase the nanofat fraction of the harvested fat emulsion as it passes through the filter element 72 while simultaneously removing particles suspended in the harvested fat emulsion that are too large to pass through the openings in the filter element 72. The removed particles are retained in the conditioning chamber 58 as a filter cake similar to that shown in FIG. 19.

The portion of the harvested fat emulsion that passes through the filter element 72 is termed a sized fat emulsion and preferably has a substantially higher nanofat concentration than the contents of the conditioning chamber 58. After the sized fat emulsion passes through the filter element 72, it exits the conditioning chamber 58 and correspondingly the conditioning vessel 12 via the Luer coupler 60 and is displaced into the fluid retention chamber of the barrel 16 of the transfer syringe 14b via the Luer coupler 26. The practitioner continues applying the pulling force to the plunger 18 of the transfer syringe 14b, thereby continuing displacement of the plunger 18 in the outward expansion direction until substantially all of the harvested fat emulsion except for the filter cake is withdrawn from the conditioning chamber 58 and retained in the fluid retention chamber of the transfer syringe 14b as the sized fat emulsion.

Upon recovering the sized fat emulsion from the conditioning chamber 58 in the transfer syringe 14b, the practitioner uncouples the Luer coupler 26 of the transfer syringe 14b from the Luer coupler 60 of the conditioning vessel 12. The Luer coupler 26 of the transfer syringe 14b may then be fitted with a suitable sterile cannula in the same manner as described above with respect to the fat washing method, thereby enabling the transfer syringe 14b and the sized fat emulsion contained therein to be utilized in a fat re-injection procedure on a patient. Alternatively, the sized fat emulsion can undergo further conditioning before being utilized in a fat re-injection procedure.

An alternate fat conditioning method is described hereafter that is more particularly characterized as a fat compounding method. The instant fat compounding method utilizes the above-described fat conditioning apparatus 10 including the conditioning vessel 12 and transfer syringes 14a, 14b. The fat compounding sizing method may be performed in serial combination with other fat conditioning procedures. For example, the harvested fat emulsion can be washed as described above before performing the instant compounding method on the fat fraction resulting from the fat washing method.

The instant fat compounding method has essentially the same steps as those described above with respect to the fat washing method and shown in FIGS. 14-17 except that the transfer syringe 14b is filled with an alternate material in place of the washing liquid and the transfer syringe 14a may be filled with any number of alternate fat-containing emulsions. For example, the transfer syringe 14a be filled with a harvested fat emulsion or a fat fraction resulting from washing a harvested fat emulsion. The alternate material filling the transfer syringe 14b is termed an additive material and is preferably a fluid and is more preferably a non-fat liquid that, such as platelet rich plasma (PRP). In any case, the additive material enhances the utility of the fat-containing fat emulsion in a subsequent re-injection procedure when the additive material is completely and fully mixed with the fat-containing emulsion to form a homogeneous compounded fat emulsion. As such, the additive material is retained in the compounded fat emulsion when it is re-injected into the patient.

In accordance with the instant fat compounding method, the user injects the additive material from the transfer syringe 14b into the conditioning chamber 58 in the manner shown in FIG. 17 and permits it to mix with the fat-containing emulsion previously injected therein from the transfer syringe 14a in the manner shown in FIG. 15. The user may optionally manually shake the conditioning vessel 12 for a few seconds while maintaining the connection member cap 66 and transfer syringe 14b in place to facilitate mixing the fat-containing emulsion and additive material. In any case, once the fat-containing emulsion and additive material occupy the conditioning chamber 58 and, if desired, the user has briefly shaken the mixture of the fat-containing emulsion and additive material, the connection member cap 66 is uncoupled from the Luer coupler 60 of the conditioning vessel 12 and replaced with an empty transfer syringe, e.g., the empty transfer syringe 16a or a new empty transfer syringe (not shown), in essentially the same manner as described above with respect to the fat sizing method while maintaining the transfer syringe 14b coupled with the plug 64.

Full and complete mixing of the fat-containing emulsion and additive material is effected by applying a manual pulling force to the plunger 18 of the empty transfer syringe, thereby drawing the mixture of fat-containing emulsion and additive material residing in the conditioning chamber 58 across the upstream filter element 72 in the filter cartridge 68 toward the Luer coupler 60 of the conditioning vessel 58. The filter element 72 may be the same filter element as employed in the above-described fat washing method or any other suitable filter element within the purview of the ordinary artisan in accordance with the teaching herein to facilitate full and complete mixing of the fat-containing emulsion and additive material with one another as they pass through the filter element 72 while simultaneously removing particles suspended in the fat-containing emulsion that are too large to pass through the openings in the filter element 72. The removed particles are retained in the conditioning chamber 58 as a filter cake similar to that shown in FIG. 19.

It is apparent that passing the mixture of fat-containing emulsion and additive material though the upstream filter element 72 enhances contacting between the fat-containing emulsion and liquid additive and completes their mixing to form the homogenous compounded fat emulsion. Upon recovering the compounded fat emulsion in the transfer syringe from the conditioning chamber 58, the practitioner uncouples the Luer coupler 26 of the transfer syringe from the Luer coupler 60 of the conditioning vessel 12 in the same manner as described above with respect to the fat sizing method and the compounded fat emulsion contained in the transfer syringe is suitable for use in a fat re-injection procedure on a patient. Alternatively, the compounded fat emulsion can undergo further conditioning before being utilized in a fat re-injection procedure.

While the forgoing preferred embodiments of the invention have been described and shown, it is understood that alternatives and modifications within the purview of the ordinary artisan, such as those suggested and others, may be made thereto and fall within the scope of the invention.

We claim:
1. A fat conditioning method comprising the steps of:
injecting a harvested fat emulsion into a conditioning chamber of a conditioning vessel, wherein said conditioning chamber has a variable volume and is bounded on a first conditioning chamber end by a fixed end of said conditioning vessel and is variably bounded on a second conditioning chamber end by a plug displacable within said conditioning vessel;
displacing said plug in an outward expansion direction within said conditioning vessel in response to injection of said harvested fat emulsion into said conditioning chamber, thereby expanding said variable volume of said conditioning chamber;
injecting a washing liquid into said conditioning chamber;
displacing said plug in said outward expansion direction within said conditioning vessel in response to injection of said washing liquid into said conditioning chamber, thereby expanding said variable volume of said conditioning chamber;
mixing said harvested fat emulsion and said washing liquid in said conditioning chamber to produce a mixture of said harvested fat emulsion and said washing liquid;
stratifying said mixture into a contaminant-lean, fat fraction and a contaminant-rich, wash liquid-rich remainder fraction; and
recovering said fat fraction substantially free of said remainder fraction from said conditioning chamber.

2. The method of claim 1 further comprising removing said remainder fraction from said conditioning chamber before recovering said fat fraction.

3. The method of claim 2, wherein said fixed end of said conditioning vessel has a selectively blocked port or unblocked port formed therein and said remainder fraction is removed from said conditioning chamber by selecting said unblocked port and discharging said remainder fraction from said conditioning chamber via said unblocked port.

4. The method of claim 3 further comprising passing said remainder fraction through a filter element fixably positioned in said conditioning chamber at said fixed end of said conditioning vessel and thereafter discharging said remainder fraction from said conditioning chamber.

5. The method of claim 4 further comprising passing said remainder fraction through a porous screen supporting said filter element, wherein said porous screen is fixably stacked against said filter element in said conditioning chamber downstream of said filter element.

6. The method of claim 1, wherein said fat fraction is recovered from said conditioning chamber through said plug.

7. The method of claim 6, wherein said fat fraction is recovered from said conditioning chamber by drawing said fat fraction through said plug into said washing liquid-containing transfer syringe or an other transfer syringe engaging said plug.

8. The method of claim 1, wherein said harvested fat emulsion is injected into said conditioning chamber through said plug from a harvested fat emulsion-containing transfer syringe engaging said plug.

9. The method of claim 1, wherein said washing liquid is injected into said conditioning chamber through said plug from a washing liquid-containing transfer syringe engaging said plug.

10. The method of claim 1, wherein mixing of said harvested fat emulsion and said washing liquid in said conditioning chamber is facilitated by agitation of said harvested fat emulsion and said washing liquid in said conditioning chamber.

11. The method of claim 1, wherein said fixed end of said conditioning vessel has a selectively blocked port or unblocked port formed therein and said harvested fat emulsion is injected into said conditioning chamber after selecting said blocked port to prevent fluid passage therethrough.

12. The method of claim 1, wherein said fixed end of said conditioning vessel has a selectively blocked port or unblocked port formed therein and said washing liquid is injected into said conditioning chamber after selecting said blocked port to prevent fluid passage therethrough.

13. A fat conditioning method comprising the steps of:
injecting a harvested fat emulsion into a conditioning chamber of a conditioning vessel, through a plug displacable within said conditioning vessel from a harvested fat emulsion-containing transfer syringe engaging said plug, wherein said conditioning chamber has a variable volume and is bounded on a first conditioning chamber end by a fixed end of said conditioning vessel having a selectively blocked port or unblocked port formed therein and is variably bounded on a second conditioning chamber end by said plug and wherein said harvested fat emulsion is injected into said conditioning chamber after selecting said blocked port to prevent fluid passage therethrough;
displacing said plug in an outward expansion direction within said conditioning vessel in response to injection of said harvested fat emulsion into said conditioning chamber, thereby expanding said variable volume of said conditioning chamber;
injecting a washing liquid into said conditioning chamber through said plug from a washing liquid-containing transfer syringe engaging said plug, wherein said washing liquid is injected into said conditioning chamber while maintaining selection of said blocked port to prevent fluid passage therethrough;
displacing said plug in said outward expansion direction within said conditioning vessel in response to injection of said washing liquid into said conditioning chamber, thereby expanding said variable volume of said conditioning chamber;
mixing said harvested fat emulsion and said washing liquid in said conditioning chamber to produce a mixture of said harvested fat emulsion and said washing liquid;
stratifying said mixture into a contaminant-lean fat fraction and a contaminant-rich, wash liquid-rich remainder fraction;
passing said remainder fraction through a filter element fixably positioned in said conditioning chamber at said fixed end of said conditioning vessel upstream of said unblocked port;
removing said remainder fraction from said conditioning chamber via said unblocked port; and
recovering said fat fraction substantially free of said remainder fraction from said conditioning chamber by drawing said fat fraction through said plug into said washing liquid-containing transfer syringe or an other transfer syringe engaging said plug.

14. The method of claim 13 further comprising converting said harvested fat emulsion-containing transfer syringe to said washing liquid-containing syringe before said washing liquid is placed in said conditioning chamber by placing said washing liquid in said harvested fat emulsion-containing transfer syringe after said harvested fat emulsion contained therein is injected into said into said conditioning chamber.

15. A fat conditioning method comprising the steps of:
inserting a harvested fat emulsion-containing transfer syringe into an interior of a conditioning vessel, wherein said conditioning vessel has a closed first end and an open second end opposite said closed first end, said harvested fat emulsion-containing transfer syringe is inserted into said interior via said open second end, said closed first end has a selectively blocked port or unblocked port extending therethrough, said unblocked port enables fluid communication between said interior and an exterior of said conditioning vessel via said closed first end and said blocked port prevents fluid communication between said interior and said exterior via said closed first end;
engaging a plug positioned within said interior with said harvested fat emulsion-containing transfer syringe, wherein said interior contains a conditioning chamber having a first conditioning chamber end at said closed first end of said conditioning vessel and a second conditioning chamber end at said plug, and wherein said plug is sidably displaceable with said conditioning vessel such that said conditioning chamber has a variable volume;
selecting said blocked port;
injecting a harvested fat emulsion in said harvested fat emulsion-containing transfer syringe through said plug into said conditioning chamber;
displacing said plug in an outward expansion direction within said conditioning vessel in response to injection of said harvested fat emulsion into said conditioning chamber, thereby expanding said variable volume of said conditioning chamber;
placing a washing liquid in said conditioning chamber;
displacing said plug in said outward expansion direction within said conditioning vessel in response to injection of said washing liquid into said conditioning chamber, thereby expanding said variable volume of said conditioning chamber;
mixing said harvested fat emulsion and said washing liquid in said conditioning chamber to produce a mixture of said harvested fat emulsion and said washing liquid;
stratifying said mixture into a contaminant-lean, fat fraction and a contaminant-rich, wash liquid-rich remainder fraction; and
recovering said fat fraction substantially free of said remainder fraction from said conditioning chamber.

16. The method of claim 15 further comprising passing said remainder fraction through a filter element fixably positioned in said conditioning chamber at said fixed end of said conditioning vessel and thereafter discharging said remainder fraction from said conditioning chamber via said unblocked port.

17. The method of claim 16 further comprising passing said remainder fraction through a porous screen supporting said filter element, wherein said porous screen is fixably stacked against said filter element in said conditioning chamber downstream of said filter element.

18. The method of claim 15, wherein said washing liquid is injected into said conditioning chamber through said plug from a washing liquid-containing transfer syringe engaging said plug.

19. The method of claim 18 further comprising converting said harvested fat emulsion-containing transfer syringe to said washing liquid-containing syringe before said washing liquid is placed in said conditioning chamber by placing said washing liquid in said harvested fat emulsion-containing transfer syringe after said harvested fat emulsion contained therein is injected into said into said conditioning chamber.

20. The method of claim 15, wherein said fat fraction is recovered from said conditioning chamber by drawing said fat fraction through said plug into said washing liquid-containing transfer syringe or an other transfer syringe engaging said plug.

* * * * *